United States Patent
Newell et al.

(10) Patent No.: US 10,043,284 B2
(45) Date of Patent: Aug. 7, 2018

(54) SYSTEMS AND METHODS FOR REAL-TIME TUMOR TRACKING

(71) Applicant: Varian Medical Systems, Palo Alto, CA (US)

(72) Inventors: Laurence J. Newell, Mercer Island, WA (US); Stephen Phillips, Woodinville, WA (US); Raymond Kraft, Seattle, WA (US); Sun-Kai Lin, Seattle, WA (US)

(73) Assignee: Varian Medical Systems, Inc., Palo Alto, CA (US)

( * ) Notice: Subject to any disclaimer, the term of this patent is extended or adjusted under 35 U.S.C. 154(b) by 476 days.

(21) Appl. No.: 14/272,382

(22) Filed: May 7, 2014

(65) Prior Publication Data
US 2015/0324967 A1 Nov. 12, 2015

(51) Int. Cl.
*G06T 7/00* (2017.01)
*G06T 7/277* (2017.01)
(Continued)

(52) U.S. Cl.
CPC ............ *G06T 7/277* (2017.01); *G06T 7/0012* (2013.01); *G06T 7/246* (2017.01); *G06T 7/70* (2017.01);
(Continued)

(58) Field of Classification Search
CPC .................. G06T 7/004; G06T 7/0012; G06T 2207/30096; G06T 2210/12;
(Continued)

(56) References Cited

U.S. PATENT DOCUMENTS 3,349,242 A 10/1967 Braestrup
3,577,160 A 5/1971 White
(Continued)

FOREIGN PATENT DOCUMENTS

DE 19914455 10/2000
EP 0531081 A1 3/1993
(Continued)

OTHER PUBLICATIONS

Hong, Julian C., Neville CW Eclov, Yao Yu, Aarti K. Rao, Sonja Dieterich, Quynh-Thu Le, Maximilian Diehn et al. "Migration of implanted markers for image-guided lung tumor stereotactic ablative radiotherapy." Journal of Applied Clinical Medical Physics 14, No. 2 (2013).*
(Continued)

*Primary Examiner* — Carol Wang
(74) *Attorney, Agent, or Firm* — Perkins Coie LLP

(57) ABSTRACT

Various embodiments disclose systems and methods for tracking regions (e.g., tumor locations) within living organisms. Some embodiments provide real-time, highly accurate, low latency measurements of tumor location even as the tumor moves with internal body motions. Such measurements may be suitable for closed-loop radiation delivery applications where radiation therapy may be continuously guided to the tumor site even as the tumor moves. Tumor motion may be associated with periodic motion (e.g., respiratory, cardiac) or aperiodic motion (e.g., gross patient motion, internal bowel motion). Various embodiments facilitate accurate radiation delivery to tumor sites exhibiting significant motion, e.g., lung, breast, and liver tumors.

23 Claims, 14 Drawing Sheets

(51) Int. Cl.
  *G06T 7/70* (2017.01)
  *G06T 7/246* (2017.01)
  *A61B 34/20* (2016.01)

(52) U.S. Cl.
  CPC ............... *A61B 2034/2051* (2016.02); *G06T 2207/30081* (2013.01); *G06T 2207/30096* (2013.01); *G06T 2207/30204* (2013.01)

(58) Field of Classification Search
  CPC .......... G06K 2017/0045; A61B 5/0002; A61B 5/742; A61B 5/7275; A61B 5/1115; A61B 5/6814; A61B 5/14503; A61B 5/72; A61B 5/055; A61B 5/113; A61B 5/4381; A61B 5/4836; A61B 5/11; A61B 5/1113; A61B 5/1128; A61B 2017/00119; A61B 2090/374; A61B 2018/00577
  See application file for complete search history.

(56) References Cited

U.S. PATENT DOCUMENTS

| | | | |
|---|---|---|---|
| 3,967,161 A | 6/1976 | Lichtblau | |
| 3,969,629 A | 7/1976 | McIntyre | |
| 4,023,167 A | 5/1977 | Wahlstrom | |
| 4,114,601 A | 9/1978 | Abels | |
| 4,123,749 A | 10/1978 | Hartmann et al. | |
| 4,127,110 A | 11/1978 | Bullara | |
| 4,160,971 A | 7/1979 | Jones et al. | |
| 4,222,374 A | 9/1980 | Sampson et al. | |
| 4,260,990 A | 4/1981 | Lichtblau | |
| 4,393,872 A | 7/1983 | Reznik et al. | |
| 4,618,822 A | 10/1986 | Hansen | |
| 4,633,250 A | 12/1986 | Anderson, III et al. | |
| 4,643,196 A | 2/1987 | Tanaka et al. | |
| 4,696,287 A | 9/1987 | Hortmann et al. | |
| 4,745,401 A | 5/1988 | Montean | |
| 4,787,098 A | 11/1988 | Silver | |
| 4,795,995 A | 1/1989 | Eccleston et al. | |
| 4,799,495 A | 1/1989 | Hawkins et al. | |
| 4,909,789 A | 3/1990 | Taguchi et al. | |
| 4,936,823 A | 6/1990 | Colvin et al. | |
| 4,945,914 A | 8/1990 | Allen | |
| 4,994,079 A | 2/1991 | Genese et al. | |
| 5,018,178 A | 5/1991 | Katsumata et al. | |
| 5,031,634 A | 7/1991 | Simon | |
| 5,057,095 A | 10/1991 | Fabian | |
| 5,062,847 A | 11/1991 | Barnes | |
| 5,095,224 A | 3/1992 | Renger | |
| 5,099,845 A | 3/1992 | Besz et al. | |
| 5,107,862 A | 4/1992 | Fabian et al. | |
| 5,142,292 A | 8/1992 | Chang | |
| 5,152,776 A | 10/1992 | Pinchuk | |
| 5,170,055 A | 12/1992 | Carroll et al. | |
| 5,239,474 A | 8/1993 | Eaton, Jr. et al. | |
| 5,325,873 A | 7/1994 | Hirschi et al. | |
| 5,353,804 A | 10/1994 | Kornberg et al. | |
| 5,391,199 A | 2/1995 | Ben-Haim | |
| 5,409,004 A | 4/1995 | Sloan | |
| 5,423,334 A | 6/1995 | Jordan | |
| 5,425,367 A | 6/1995 | Shapiro et al. | |
| 5,425,382 A | 6/1995 | Golden et al. | |
| 5,431,161 A | 7/1995 | Ryals et al. | |
| 5,446,548 A | 8/1995 | Gerig et al. | |
| 5,509,900 A | 4/1996 | Kirkman | |
| 5,528,651 A | 6/1996 | Leksell et al. | |
| 5,545,993 A * | 8/1996 | Taguchi ............. G01R 33/5676 324/307 |
| 5,557,690 A * | 9/1996 | O'Gorman ........... G06K 9/3216 348/87 |
| 5,626,630 A | 5/1997 | Markowitz et al. | |
| 5,638,819 A | 6/1997 | Manwaring et al. | |
| 5,651,043 A | 7/1997 | Tsuyuki et al. | |
| 5,680,106 A | 10/1997 | Schrott et al. | |
| 5,697,384 A | 12/1997 | Miyawaki et al. | |
| 5,707,362 A | 1/1998 | Yoon | |
| 5,707,390 A | 1/1998 | Bonutti | |
| 5,711,299 A | 1/1998 | Manwaring et al. | |
| 5,713,847 A | 2/1998 | Howard, III et al. | |
| 5,727,552 A | 3/1998 | Ryan | |
| 5,731,996 A | 3/1998 | Gilbert | |
| 5,733,322 A | 3/1998 | Starkebaum | |
| 5,735,795 A | 4/1998 | Young et al. | |
| 5,748,767 A | 5/1998 | Raab | |
| 5,754,623 A | 5/1998 | Seki | |
| 5,757,881 A | 5/1998 | Hughes | |
| 5,764,052 A | 6/1998 | Renger | |
| 5,769,861 A | 6/1998 | Vilsmeier | |
| 5,810,851 A | 9/1998 | Yoon | |
| 5,815,076 A | 9/1998 | Herring | |
| 5,840,148 A | 11/1998 | Campbell et al. | |
| 5,868,673 A | 2/1999 | Vesely | |
| 5,879,297 A | 3/1999 | Haynor et al. | |
| 5,910,144 A | 6/1999 | Hayashi | |
| 5,928,137 A | 7/1999 | Green | |
| 5,951,481 A | 9/1999 | Evans | |
| 5,957,934 A | 9/1999 | Rapoport | |
| 5,989,265 A | 11/1999 | Bouquet De La Joliniere et al. | |
| 6,026,818 A | 2/2000 | Blair et al. | |
| 6,031,533 A | 2/2000 | Peddada et al. | |
| 6,059,734 A | 5/2000 | Yoon | |
| 6,061,644 A | 5/2000 | Leis | |
| 6,067,465 A | 5/2000 | Foo et al. | |
| 6,076,008 A | 6/2000 | Bucholz | |
| 6,081,238 A | 6/2000 | Alicot | |
| 6,082,366 A | 7/2000 | Andra et al. | |
| 6,118,848 A | 9/2000 | Reiffel | |
| 6,144,875 A | 11/2000 | Schweikard et al. | |
| 6,161,009 A | 12/2000 | Skurdal et al. | |
| 6,198,963 B1 | 3/2001 | Haim et al. | |
| 6,222,544 B1 | 4/2001 | Tarr et al. | |
| 6,246,900 B1 | 6/2001 | Cosman et al. | |
| 6,289,233 B1 | 9/2001 | Dumoulin et al. | |
| 6,307,473 B1 | 10/2001 | Zampini et al. | |
| 6,325,758 B1 | 12/2001 | Carol et al. | |
| 6,353,655 B1 | 3/2002 | Siochi | |
| 6,359,959 B1 | 3/2002 | Butler et al. | |
| 6,360,116 B1 | 3/2002 | Jackson, Jr. et al. | |
| 6,363,940 B1 | 4/2002 | Krag | |
| 6,371,379 B1 | 4/2002 | Dames et al. | |
| 6,377,162 B1 | 4/2002 | Delestienne et al. | |
| 6,381,485 B1 | 4/2002 | Hunter et al. | |
| 6,385,286 B1 | 5/2002 | Fitchard et al. | |
| 6,385,288 B1 | 5/2002 | Kanematsu | |
| 6,393,096 B1 | 5/2002 | Carol et al. | |
| 6,405,072 B1 | 6/2002 | Cosman | |
| 6,416,520 B1 | 7/2002 | Kynast et al. | |
| 6,484,118 B1 | 11/2002 | Govari | |
| 6,501,981 B1 | 12/2002 | Schweikard et al. | |
| 6,510,199 B1 | 1/2003 | Hughes et al. | |
| 6,526,415 B2 | 2/2003 | Smith et al. | |
| 6,535,756 B1 | 3/2003 | Simon et al. | |
| 6,650,930 B2 | 11/2003 | Ding | |
| 6,662,036 B2 | 12/2003 | Cosman | |
| 6,675,810 B2 | 1/2004 | Krag | |
| 6,690,965 B1 * | 2/2004 | Riaziat ............... A61B 6/463 378/62 |
| 6,698,433 B2 | 3/2004 | Krag | |
| 6,702,780 B1 | 3/2004 | Gilboa et al. | |
| 6,711,431 B2 | 3/2004 | Sarin et al. | |
| 6,812,842 B2 | 11/2004 | Dimmer | |
| 6,822,570 B2 | 11/2004 | Dimmer et al. | |
| 6,838,990 B2 | 1/2005 | Dimmer | |
| 6,882,947 B2 | 4/2005 | Levin | |
| 6,918,919 B2 | 7/2005 | Krag | |
| 6,934,356 B1 | 8/2005 | Satheesan et al. | |
| 6,937,696 B1 | 8/2005 | Mostafavi | |
| 6,961,405 B2 | 11/2005 | Scherch | |
| 6,977,504 B2 | 12/2005 | Wright et al. | |
| 6,980,679 B2 * | 12/2005 | Jeung ................. A61B 5/1127 382/107 |
| 6,993,112 B2 | 1/2006 | Hesse | |
| 6,999,555 B2 | 2/2006 | Mori | |
| 6,999,819 B2 | 2/2006 | Swoyer et al. | |

(56) References Cited

U.S. PATENT DOCUMENTS

| | | |
|---|---|---|
| 7,026,927 B2 | 4/2006 | Wright et al. |
| 7,027,707 B2 | 4/2006 | Imaki |
| 7,135,978 B2 | 11/2006 | Gisselberg et al. |
| 7,142,905 B2 | 11/2006 | Slayton et al. |
| 7,154,991 B2 | 12/2006 | Earnst et al. |
| 7,174,201 B2 | 2/2007 | Govari et al. |
| 7,176,798 B2 | 2/2007 | Dimmer et al. |
| 7,206,626 B2 | 4/2007 | Quaid, III |
| 7,206,627 B2 | 4/2007 | Abovitz et al. |
| 7,213,009 B2 | 5/2007 | Pestotnik et al. |
| 7,221,733 B1 | 5/2007 | Takai et al. |
| 7,241,283 B2 | 7/2007 | Putz |
| 7,280,863 B2 | 10/2007 | Shachar |
| 7,289,599 B2 | 10/2007 | Seppi et al. |
| 7,289,839 B2 | 10/2007 | Dimmer et al. |
| 7,447,643 B1 | 11/2008 | Olson et al. |
| 7,557,353 B2 | 7/2009 | Black et al. |
| 7,587,234 B2 | 9/2009 | Owens et al. |
| 7,606,405 B2 | 10/2009 | Sawyer et al. |
| 7,657,301 B2 | 2/2010 | Mate et al. |
| 7,657,302 B2 | 2/2010 | Mate et al. |
| 7,657,303 B2 | 2/2010 | Mate et al. |
| 7,684,849 B2 | 3/2010 | Wright et al. |
| 7,729,742 B2 | 6/2010 | Govari |
| 7,747,307 B2 | 6/2010 | Wright et al. |
| 7,899,513 B2 | 3/2011 | Phillips et al. |
| 8,050,774 B2 | 11/2011 | Kveen et al. |
| 8,095,203 B2 | 1/2012 | Wright et al. |
| 8,121,368 B2* | 2/2012 | Wiersma ............... G06T 7/2046 382/128 |
| 8,197,494 B2 | 6/2012 | Jaggi et al. |
| 8,239,005 B2 | 8/2012 | Wright et al. |
| 9,237,860 B2 | 1/2016 | Parikh et al. |
| 2002/0049362 A1 | 4/2002 | Ding |
| 2002/0065461 A1 | 5/2002 | Cosman |
| 2002/0165443 A1 | 11/2002 | Mori |
| 2002/0183611 A1 | 12/2002 | Fishbein et al. |
| 2002/0188194 A1 | 12/2002 | Cosman |
| 2002/0193685 A1* | 12/2002 | Mate ................... A61N 5/1049 600/424 |
| 2003/0002621 A1 | 1/2003 | Hughes et al. |
| 2003/0023161 A1 | 1/2003 | Govari et al. |
| 2003/0052785 A1 | 3/2003 | Gisselberg et al. |
| 2003/0070682 A1 | 4/2003 | Wilson et al. |
| 2003/0088178 A1 | 5/2003 | Owens et al. |
| 2003/0120150 A1 | 6/2003 | Govari |
| 2003/0125616 A1 | 7/2003 | Black et al. |
| 2003/0125622 A1 | 7/2003 | Schweikard et al. |
| 2003/0181794 A1 | 9/2003 | Rini et al. |
| 2003/0184285 A1* | 10/2003 | Anderson ................ A61B 5/06 324/207.17 |
| 2003/0192557 A1 | 10/2003 | Krag et al. |
| 2003/0206610 A1 | 11/2003 | Collins |
| 2003/0206614 A1 | 11/2003 | Kendrick et al. |
| 2003/0212412 A1 | 11/2003 | Dillard et al. |
| 2004/0013855 A1 | 1/2004 | Chen et al. |
| 2004/0019274 A1 | 1/2004 | Galloway et al. |
| 2004/0034355 A1 | 2/2004 | Govari et al. |
| 2004/0068182 A1 | 4/2004 | Misra |
| 2004/0096033 A1 | 5/2004 | Seppi et al. |
| 2004/0116804 A1 | 6/2004 | Mostafavi |
| 2004/0122311 A1 | 6/2004 | Cosman |
| 2004/0122608 A1 | 6/2004 | Levin |
| 2004/0125916 A1 | 7/2004 | Herron et al. |
| 2004/0127787 A1 | 7/2004 | Dimmer et al. |
| 2004/0133101 A1 | 7/2004 | Mate et al. |
| 2004/0133887 A1 | 7/2004 | Herle et al. |
| 2004/0158146 A1 | 8/2004 | Mate et al. |
| 2004/0176931 A1 | 9/2004 | Wright et al. |
| 2005/0059884 A1 | 3/2005 | Krag |
| 2005/0059887 A1 | 3/2005 | Mostafavi et al. |
| 2005/0077459 A1 | 4/2005 | Engler et al. |
| 2005/0085710 A1 | 4/2005 | Earnst et al. |
| 2005/0101824 A1 | 5/2005 | Stubbs et al. |
| 2005/0140372 A1 | 6/2005 | Wright et al. |
| 2005/0151649 A1 | 7/2005 | Wright et al. |
| 2005/0152495 A1 | 7/2005 | Hesse |
| 2005/0154280 A1 | 7/2005 | Wright et al. |
| 2005/0154283 A1 | 7/2005 | Wright et al. |
| 2005/0154284 A1 | 7/2005 | Wright et al. |
| 2005/0154293 A1 | 7/2005 | Gisselberg et al. |
| 2005/0195084 A1 | 9/2005 | Dimmer et al. |
| 2005/0201510 A1 | 9/2005 | Mostafavi |
| 2005/0203431 A1 | 9/2005 | Brodnick et al. |
| 2005/0234332 A1 | 10/2005 | Murphy |
| 2005/0251111 A1 | 11/2005 | Saito et al. |
| 2005/0261570 A1 | 11/2005 | Mate et al. |
| 2006/0052694 A1 | 3/2006 | Phillips et al. |
| 2006/0058648 A1* | 3/2006 | Meier ................... A61N 5/1049 600/436 |
| 2006/0063999 A1 | 3/2006 | Herron et al. |
| 2006/0074301 A1 | 4/2006 | Meier et al. |
| 2006/0074302 A1 | 4/2006 | Meier et al. |
| 2006/0078086 A1 | 4/2006 | Riley et al. |
| 2006/0079764 A1 | 4/2006 | Wright et al. |
| 2006/0093089 A1* | 5/2006 | Vertatschitsch ....... A61N 5/1049 378/65 |
| 2006/0100509 A1 | 5/2006 | Wright et al. |
| 2006/0147100 A1* | 7/2006 | Fitzpatrick ........... G06K 9/6211 382/131 |
| 2006/0173294 A1 | 8/2006 | Ein-Gal |
| 2007/0153972 A1 | 7/2007 | Fujishige et al. |
| 2007/0161884 A1 | 7/2007 | Black et al. |
| 2008/0039746 A1 | 2/2008 | Hissong et al. |
| 2008/0226149 A1 | 9/2008 | Wischmann et al. |
| 2008/0287781 A1 | 11/2008 | Revie et al. |
| 2010/0282983 A1 | 11/2010 | Wright et al. |
| 2012/0138801 A1* | 6/2012 | Vanderpohl .......... A61B 5/0077 250/349 |
| 2015/0085072 A1 | 3/2015 | Yan et al. |

FOREIGN PATENT DOCUMENTS

| | | |
|---|---|---|
| FR | 2635259 | 2/1990 |
| FR | 2686499 | 7/1993 |
| JP | 07-313515 | 12/1995 |
| JP | 8-166446 | 6/1996 |
| JP | 2004-154548 | 6/2000 |
| JP | 2001-008947 | 1/2001 |
| WO | WO-95/25475 | 9/1995 |
| WO | 9608208 | 3/1996 |
| WO | WO-97/12553 | 4/1997 |
| WO | WO-98/30166 | 7/1998 |
| WO | WO-98/38908 | 9/1998 |
| WO | WO-98/40026 A | 9/1998 |
| WO | WO-99/30182 | 6/1999 |
| WO | WO-99/33406 | 7/1999 |
| WO | WO-99/40869 | 8/1999 |
| WO | WO-9953966 | 10/1999 |
| WO | WO-99/58044 | 11/1999 |
| WO | WO-99/58065 | 11/1999 |
| WO | WO-00/24332 | 5/2000 |
| WO | WO-00/38579 | 7/2000 |
| WO | WO-00/51514 | 9/2000 |
| WO | WO 00/53115 | 9/2000 |
| WO | WO-00/65989 A | 11/2000 |
| WO | WO-01/034049 | 5/2001 |
| WO | WO-01/54765 | 8/2001 |
| WO | WO-02/19908 | 3/2002 |
| WO | WO-02/39917 | 5/2002 |
| WO | WO-02/39918 | 5/2002 |
| WO | WO-02/100485 A1 | 12/2002 |
| WO | 0353270 | 7/2003 |
| WO | WO-04/060177 | 7/2004 |
| WO | WO-04/060475 | 7/2004 |
| WO | 2005067792 A1 | 7/2005 |
| WO | WO-05/067792 | 7/2005 |
| WO | WO-2006002396 | 1/2006 |
| WO | 2006020377 A2 | 2/2006 |
| WO | WO-06/023055 | 3/2006 |

(56) References Cited

FOREIGN PATENT DOCUMENTS

| WO | WO-2007035798 | 3/2007 |
|---|---|---|
| WO | WO-2009149409 | 12/2009 |

OTHER PUBLICATIONS

Jiang, Steve B. "Radiotherapy of mobile tumors." In Seminars in radiation oncology, vol. 16, No. 4, pp. 239-248. WB Saunders, 2006.*
International Search Report completed for PCT/US02/29390 dated Jan. 14, 2003, 6 pages.
European Search Report for European Patent Application No. 03814943.1 dated Apr. 1, 2008, 8 pages.
International Search Report and Written Opinion for PCT/US03/41140 dated Jun. 1, 2007, 11 pages.
Kirsch S. et al., "Real Time Tracking of Tumor Positions for Precision Irradiation", Elsevier Science B. V., Jun. 24, 1998, pp. 262-264, 3 pages.
Final Office Action, U.S. Appl. No. 09/877,498, Applicant: Calypso Medical Technologies, Inc., dated Feb. 14, 2006, 7 pages.
Decision on Appeal, U.S. Appl. No. 09/877,498, Applicant: Calypso Medical Technologies, Inc., dated May 27, 2009, 16 pages.
Hsiao, K. "Fast Multi-Axis Tracking of Magnetically-Resonant Passive Tags: Methods and Applications," Feb. 2001, Massachusetts Institute of Technology, Dept. of Electrical Engineering and Computer Science, pp. 1-107.
International Preliminary Examination Report for PCT/US02/17876, dated Jul. 8, 2004, Applicant: Calypso Medical Technologies, Inc., 4 pages.
European Search Report for European Application No. 10185512 dated Jun. 28, 2011, 3 pages.
International Search Report and Written Opinion for PCT/US09/046494, dated Jul. 28, 2009, 10 pages.
European Search Report for European Application No. 05763751, Applicant: Calypso Medical, Inc., dated Feb. 21, 2008, 5 pages.
European Search Report for European Application No. 05763751, Applicant: Calypso Medical, Inc., dated Sep. 18, 2008, 5 pages.
Sharp et al., "Prediction of Respiratory Tumour Motion for Real-Time Image-Guided Radiotherapy," published Jan. 16, 2004, IPO Publishing Ltd., pp. 425-440, 16 pages.
P.G. Seiler, et al, "A Novel Tracking Technique for the Continuous Precise Measurement of Tumour Positions in Conformal Therapy," Jun. 7, 2000, IOP Publishing Ltd., Phys. Med. Biol., vol. 45, pp. N103-N110, 8 pages.
International Search Report for PCT/US05/22374 dated Apr. 25, 2007, 1 page.
Written Opinion for PCT/US05/022374 dated Apr. 25, 2007, 5 pages.
International Search Report for PCT/US05/01070 dated Jun. 21, 2005, 1 page.
Written Opinion for PCT/US05/01070 dated Jun. 21, 2005, 3 pages.
International Search Report for PCT/US05/022568 dated Feb. 16, 2007, 1 page.
Written Opinion for PCT/US05/022568 dated Feb. 16, 2007, 4 pages.
International Search Report for PCT/US06/036585 dated Jun. 23, 2008, 1 page.
Written Opinion for PCT/US06/036585 dated Jun. 23, 2008, 3 pages.
International Search Report for PCT/US09/046494 dated Jul. 28, 2009, 1 page.
Written Opinion for PCT/US09/046494 dated Jul. 28, 2009, 8 pages.
Seppenwoolde et al, Precise and real-time measurement of 3D tumor motion in lung due to breathing and heartbeat, measured during radiotherapy, Int. J. Radiat. Oncol. Biol. Phys. Jul. 15, 2002, 53, pp. 822-834.
Beyer, Thomas et al. "Dual-modality PET/CT Imaging: the effect of respiratory motion on combined image quality in clinical oncology." European journal of nuclear medicine and molecular imaging 30.4 (2003): 588-596.
Low, Daniel A., et al. "A method for the reconstruction of four-dimensional synchronized CT scans acquired during free breathing." Medical physics 30.6 (2003) 1254-1263.
Wolthaus, J. W. H., et al. "Fusion of respiration-correlated PET and CT scans: correlated lung tumour motion in anatomical and functional scans." Physics in medicine and biology 50.7 (2005): 1569.
Hong, Julian C. et al., "Migration of implanted markers for image-guided lung tumor sterotactic ablative radiotherapy", Journal of applied Clinical Medical Physics, 14, No. 2 (2013).
Wen, Jie. "Electromagnetic Tracking for Medical Imaging." Washington University in St. Louis. Jan. 2010. pp. 1-82.

* cited by examiner

| Latency Component | Mean Latency 3B mode | Mean Latency 2B mode | Comments |
|---|---|---|---|
| ½ Measurement Integration Time | 40 ms | 40 ms | Duration from effective time of last measurement until measurement is complete |
| FE to FEC Transfer Time | 20 ms | 20 ms | Time required to transfer measurement results from FPGAs to TS |
| Processing Time | 38 ms | 38 ms | Average time required to TS to localize most recent measurement, compute target position and publish results to DGI |
| Algorithmic | 162 ms | 462 ms | Average latency due to measurement averaging, calibration dead time, etc. |
| Total | 260 ms | 560 ms | Total Mean Latency for beam hold |

*FIG. 3*

| Latency Component | Mean Latency 2B / 3B Mode | Comments |
| --- | --- | --- |
| 1/2 Measurement Integration Time | 16ms | Duration from effective time of last measurement until measurement is complete |
| FE to FEC Transfer Time | 12ms | Time required to transfer measurement results from FPGAs to Tracking System |
| Processing Time | 13ms | Average time required for Tracking System to localize most recent measurement, compute target position and publish results to DGI |
| Algorithmic | 0ms / 80ms | Average latency due to measurement averaging. Beam-hold assertion is governed by the unsmoothed signal (first one to exit the volume), which has zero latency. Beam-hold deassertion (beam-enable) is governed by the smoothed signal (last one to re-enter the volume), which uses the previous two samples causing a latency of 80ms. |
| Total | 41ms / 121ms | Total Mean Latency for Beam-Hold / Total Mean Latency for Beam-Enable |

*FIG. 4*

SYSTEMS AND METHODS FOR REAL-TIME TUMOR TRACKING

FIELD

Various of the disclosed embodiments relate to systems and methods for locating regions of the human body, e.g., for applying real-time treatment to cancerous tumors.

BACKGROUND

Many surgical and therapeutic procedures require an accurate, up-to-date representation of a patient's localized internal regions. For example, radiation therapy has successfully treated various cancers, including prostate cancer, lung cancer, and brain cancer, by delivering radiation to a specified region in quantified dosages. While higher doses may be more effective in disrupting the cancer, higher doses may also severely damage surrounding tissue. Similarly, dispersing the radiation into healthy regions may lessen the desired effect upon the unhealthy region. Sonic and drug delivery mechanisms may suffer similar complications.

Accordingly, there is a need for accurate, near real-time representations of the present orientation and/or location of regions in a patient's body. Because the body may move with periodic (e.g., breathing) and aperiodic (e.g., digestion, patient movement) motion, reducing latency in the update representation may better ensure that therapeutic deliveries reach the desired location. Initiating delivery at a presumed location based on stale data may have adverse consequences when the region has in fact moved to a new location/orientation. Thus, hardware, software, and firmware methods for reducing latency and improving tracking accuracy are desired.

BRIEF DESCRIPTION OF THE DRAWINGS

The techniques introduced here may be better understood by referring to the following Detailed Description in conjunction with the accompanying drawings, in which like reference numerals indicate identical or functionally similar elements:

FIG. 3 is table depicting the breakdown of the system latency components for the example Xycom2® tracking station.

FIG. 4 is table depicting the breakdown of the system latency components for an example new embodiment of the tracking station.

Figure 1:
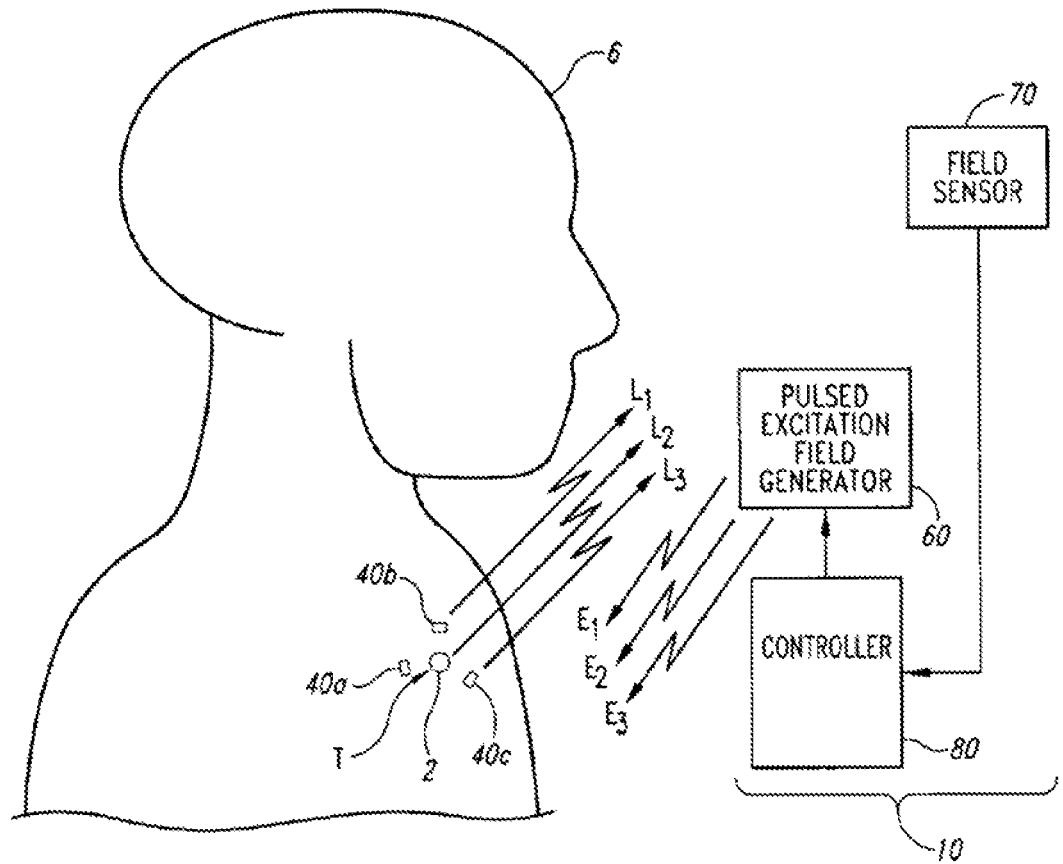
FIG. 1 is a side view schematically illustrating an example localization system and a plurality of markers/fiducials implanted in a patient as may occur in some embodiments.

The headings provided herein are for convenience only and do not necessarily affect the scope or meaning of the claimed embodiments. Further, the drawings have not necessarily been drawn to scale. For example, the dimensions of some of the elements in the figures may be expanded or reduced to help improve the understanding of the embodiments. Similarly, some components and/or operations may be separated into different blocks or combined into a single block for the purposes of discussion of some of the embodiments. Moreover, while the various embodiments are amenable to various modifications and alternative forms, specific embodiments have been shown by way of example in the drawings and are described in detail below. The intention, however, is not to limit the particular embodiments described. On the contrary, the embodiments are intended to cover all modifications, equivalents, and alternatives falling within the scope of the disclosed embodiments as defined by the appended claims.

DETAILED DESCRIPTION

Overview

Various embodiments disclose systems and methods for tracking tumors within living organisms. Some embodiments provide real-time, highly accurate, low latency measurements of tumor location even as the tumor moves with internal body motions. Such measurements may be suitable for closed-loop radiation delivery applications where radiation therapy may be continuously guided to the tumor site even as the tumor moves. Tumor motion may be associated with periodic motion (e.g., respiratory, cardiac) or aperiodic motion (e.g., gross patient motion, internal bowel motion). Various embodiments facilitate accurate radiation delivery to tumor sites exhibiting significant motion, e.g., lung, breast, and liver tumors.

Various examples of the disclosed techniques will now be described in further detail. The following description provides specific details for a thorough understanding and enabling description of these examples. One skilled in the relevant art will understand, however, that the techniques discussed herein may be practiced without many of these details. Likewise, one skilled in the relevant art will also understand that the techniques can include many other obvious features not described in detail herein. Additionally, some well-known structures or functions may not be shown or described in detail below, so as to avoid unnecessarily obscuring the relevant description.

The terminology used below is to be interpreted in its broadest reasonable manner, even though it is being used in conjunction with a detailed description of certain specific examples of the embodiments. Indeed, certain terms may even be emphasized below; however, any terminology intended to be interpreted in any restricted manner will be overtly and specifically defined as such in this section.

Example System

FIG. 1 is a block diagram of an example location determination system. For full details concerning such a system, the reader is referred to U.S. patent application Ser. No. 11/166,801 titled "SYSTEMS AND METHODS FOR REAL TIME TRACKING OF TARGETS IN RADIATION THERAPY AND OTHER MEDICAL APPLICATIONS" filed Jun. 24, 2005, the contents of which are incorporated by reference herein in their entirety for all purposes. Though examples are discussed herein with respect to human patients, one will recognize that many techniques may be applied in a veterinary context as well.

The localization system 10 and the markers 40a-c may be used to determine the location of the target 2 before, during and after radiation sessions. More specifically, the localization system 10 may determine the locations of the markers 40a-c and provide objective target position data to a memory, user interface, linear accelerator and/or other device in real time during setup, treatment, deployment, simulation, surgery, and/or other medical procedures. In some embodiments of the localization system, "real time" means that indicia of objective coordinates are provided to a user interface at (a) a sufficiently high refresh rate (i.e., frequency) such that pauses in the data are generally not humanly discernable and (b) a sufficiently low latency so as to be at least substantially contemporaneous with the measurement of the location signal. The high refresh rate may also be used to accurately sample and display relevant features of the target trajectory, e.g. in relation to a boundary, as discussed herein. An undersampled signal may miss the true displacement peaks. In other embodiments, "real time" is defined by higher frequency ranges and lower latency ranges for providing the objective data to a radiation delivery device, or in still other embodiments "real time" is defined as providing objective data responsive to the location of the markers (e.g., at a frequency that adequately tracks the location of the target in real time and/or a latency that is substantially contemporaneous with obtaining position data of the markers). Accordingly, one will construe the phrase in the context in which it is discussed.

In this example, the localization system 10 includes an excitation source 60 (e.g., a pulsed magnetic field generator), a sensor assembly 70, and a controller 80 coupled to both the excitation source 60 and the sensor assembly 70. The excitation source 60 generates an excitation energy to energize at least one of the markers 40a-c in the patient 6 (FIG. 1). The excitation source 60 may produce a pulsed magnetic field at different frequencies. For example, the excitation source 60 may frequency multiplex the magnetic field at a first frequency $E_1$ to energize the first marker 40a, a second frequency $E_2$ to energize the second marker 40b, and a third frequency $E_3$ to energize the third marker 40c. The markers may be energized in serial, rather than simultaneously, as discussed in greater detail herein in some embodiments. Exciting the markers/fiducials individually may provide better signal separation and facilitate easier implementations. In response to the excitation energy, the markers 40a-c generate location signals $L_1, L_2, L_3$ at unique response frequencies. More specifically, in this example the first marker 40a generates a first location signal $L_1$ at a first frequency in response to the excitation energy at the first frequency $E_1$, the second marker 40b generates a second location signal $L_2$ at a second frequency in response to the excitation energy at the second frequency $E_2$, and the third marker 40c generates a third location signal $L_3$ at a third frequency in response to the excitation energy at the third frequency $E_3$. In an alternative embodiment with two markers, the excitation source generates the magnetic field at frequencies $E_1$ and $E_2$, and the markers 40a-b generate location signals $L_1$ and $L_2$, respectively.

The sensor assembly 70 can include a plurality of coils to sense the location signals $L_1, L_2, L_3$ from the markers 40a-c. The sensor assembly 70 can be a flat panel having a plurality of coils that are at least substantially coplanar relative to each other. In other embodiments, the sensor assembly 70 may be a non-planar array of coils.

The controller 80 includes hardware, software or other computer-operable media containing instructions that operate the excitation source 60 to multiplex the excitation energy at the different frequencies $E_1, E_2, E_3$. For example, the controller 80 causes the excitation source 60 to generate the excitation energy at the first frequency $E_1$ for a first excitation period, and then the controller 80 causes the excitation source 60 to terminate the excitation energy at the first frequency $E_1$ for a first sensing phase during which the sensor assembly 70 senses the first location signal $L_1$ from the first marker 40a without the presence of the excitation energy at the first frequency $E_1$. The controller 80 then causes the excitation source 60 to: (a) generate the second excitation energy at the second frequency $E_2$ for a second excitation period; and (b) terminate the excitation energy at the second frequency $E_2$ for a second sensing phase during which the sensor assembly 70 senses the second location signal $L_2$ from the second marker 40b without the presence of the second excitation energy at the second frequency $E_2$. The controller 80 then repeats this operation with the third excitation energy at the third frequency $E_3$ such that the third marker 40c transmits the third location signal $L_3$ to the sensor assembly 70 during a third sensing phase. As such, the excitation source 60 wirelessly transmits the excitation energy in the form of pulsed magnetic fields at the resonant frequencies of the markers 40a-c during excitation periods, and the markers 40a-c wirelessly transmit the location signals $L_1, L_2, L_3$ to the sensor assembly 70 during sensing phases. It will be appreciated that the excitation and sensing phases can be repeated to permit averaging of the sensed signals to reduce noise.

The computer-operable media in the controller 80, or in a separate signal processor, or other computer also includes instructions to determine the absolute positions of each of the markers 40a-c in a three-dimensional reference frame. Based on signals provided by the sensor assembly 70 that correspond to the magnitude of each of the location signals $L_1, L_2, L_3$, the controller 80 and/or a separate signal processor may calculate the absolute location coordinates of each of the markers 40a-c in the three-dimensional reference frame and/or the 2-dimensional orientation of the markers. The absolute location coordinates of the markers 40a-c may be objective data that can be used to calculate the coordinates of the target in the reference frame. When multiple markers are used, the rotation of the target can also be calculated.

The localization system 10 and at least one of a marker 40 enables real time tracking of the target 2 relative to the machine isocenter or another external reference frame outside of the patient during treatment planning, set up, radiation sessions, and at other times of the radiation therapy process. In some embodiments, real time tracking refers to the collection of position and/or orientation data of the markers, determining the locations of the markers in an external reference frame, and providing an objective output in the external reference frame that is responsive to the location of the markers. The objective output is provided at a frequency that adequately tracks the target in real time and/or a latency that is at least substantially contemporaneous with collecting the position data (e.g., within a generally concurrent period of time). In some embodiments, the objective output consists of the location of the target 2 in a reference frame external to the patient (e.g., the operating room). In some real time tracking embodiments, the objective output is provided at a plurality of times during an "on-beam" period (e.g., 2, 5, 10 or more times while the beam is on).

For example, several embodiments of real time tracking are defined as determining the locations of the markers and calculating the location of the target relative to the machine isocenter at (a) a sufficiently high frequency so that pauses in representations of the target location at a user interface do not interrupt the procedure or are readily discernable by a human (e.g., sufficiently high frequency that the trajectory of the target is adequately sampled), and (b) a sufficiently low latency to be at least substantially contemporaneous with the measurement of the location signals from the markers. Alternatively, real time means that the location system 10 calculates the absolute position of each individual marker 40 and/or the location of the target at a periodicity of 1 ms to 5 seconds, or in many applications at a periodicity of approximately 10-100 ms, or in some specific applications at a periodicity of approximately 20-50 ms. In applications for user interfaces, for example, the periodicity can be 12.5 ms (i.e., a frequency of 80 Hz), 16.667 ms (60 Hz), 20 ms (50 Hz), and/or 50 ms (20 Hz).

Alternatively, real time tracking can further mean that the location system 10 provides the locations of the markers 40 and/or the target 2 to a memory device, user interface, linear accelerator or other device within a latency of 10 ms to 5 seconds from the time the localization signals were transmitted from the markers 40. In more specific applications, the location system generally provides the locations of the markers 40 and/or target 2 within a latency of about 20-50 ms. The location system 10 accordingly provides real time tracking to monitor the position of the markers 40 and/or the target 2 with respect to an external reference frame in a manner that is expected to enhance the efficacy of radiation therapy because higher radiation doses can be applied to the target and collateral effects to healthy tissue can be mitigated.

Alternatively, real-time tracking can further be defined by the tracking error. Measurements of the position of a moving target are subject to motion-induced error, generally referred to as a tracking error. According to aspects of various of the present embodiments, the localization system 10 and at least one marker 4 enable real time tracking of the target 2 relative to the machine isocenter or another external reference frame with a tracking error that is within clinically meaningful limits.

Tracking errors may arise due to two limitations exhibited by any practical measurement system, specifically (a) latency between the time the target position is sensed and the time the position measurement is made available, and (b) sampling delay due to the periodicity of measurements. For example, if a target is moving at 5 cm/s and a measurement system has a latency of 200 ms, then position measurements will be in error by 1 cm. The error in this example is due to latency alone, independent of any other measurement errors, and is simply due to the fact that the target has moved between the time its position is sensed and the time the position measurement is made available for use. If this exemplary measurement system further has a sampling periodicity of 200 ms (i.e., a sampling frequency of 5 Hz), then the peak tracking error increases to 2 cm, with an average tracking error of 1.5 cm (this example is presented with respect to a zero-order hold "analog" reconstruction and that other latencies may result from other reconstructions).

For a real time tracking system to be useful in medical applications, it is desirable to keep the tracking error within clinically meaningful limits. For example, in a system for tracking motion of a tumor in a lung for radiation therapy, it may be desirable to keep the tracking error within 5 mm. In some embodiments, the system may ensure that the error is less than 2 mm and that tracking error will be in the range of 1 mm. Acceptable tracking errors may be smaller when tracking other organs for radiation therapy. In accordance with aspects of various embodiments, real time tracking refers to measurement of target position and/or rotation with tracking errors that are within clinically meaningful limits.

The system described herein uses one or more markers to serve as registration points to characterize target location, rotation, and motion. In accordance with aspects of various embodiments, the markers may have a substantially fixed relationship with the target. If the markers did not have a substantially fixed relationship with the target another type of tracking error would be incurred. This generally requires the markers to be fixed or implanted sufficiently close to the target in order that tracking errors be within clinically meaningful limits, thus, the markers may be placed in tissue or bone that exhibits representative motion of the target. For example, with respect to the prostate, tissue that is representative of the target's motion would include tissue in close proximity or adjacent to the prostate. In the example application of tumor treatment in a prostate, the fiducials may be placed in the gland itself as the gland itself may be more rigid than the surrounding tissue. However, the prostate gland, the fiducials implanted in the gland, and the tumor sites within the gland may all move together. With respect to the prostate, tracking tissue that is a 5 cm radial distance from the target would provide representative motion that is clinically useful to the motion of the target. In accordance with alternative target tracking locations, the radial distance may be greater or lesser. Fiducials inside a prostate gland may be situated less than cm from the tumor target.

According to various embodiments, the marker motion may be a fiducial for the motion of the target. Accordingly, the marker is placed such that it moves in direct correlation to the target being tracked. Depending on the target being tracked, the direct correlation relationship between the target and the marker will vary. For example, in long bones, the marker may be placed anywhere along the bone to provide motion that directly correlates to target motion in the bone. With respect to soft tissue that moves substantially in response to the bony anatomy, for example, the head and neck, the marker may be placed in a bite block to provide fiducial motion in direct correlation with target motion. With respect to soft tissue and as discussed in detail above, the target may be placed in adjacent soft tissue to provide a fiducial having direct correlation to target motion.

Figure 2:
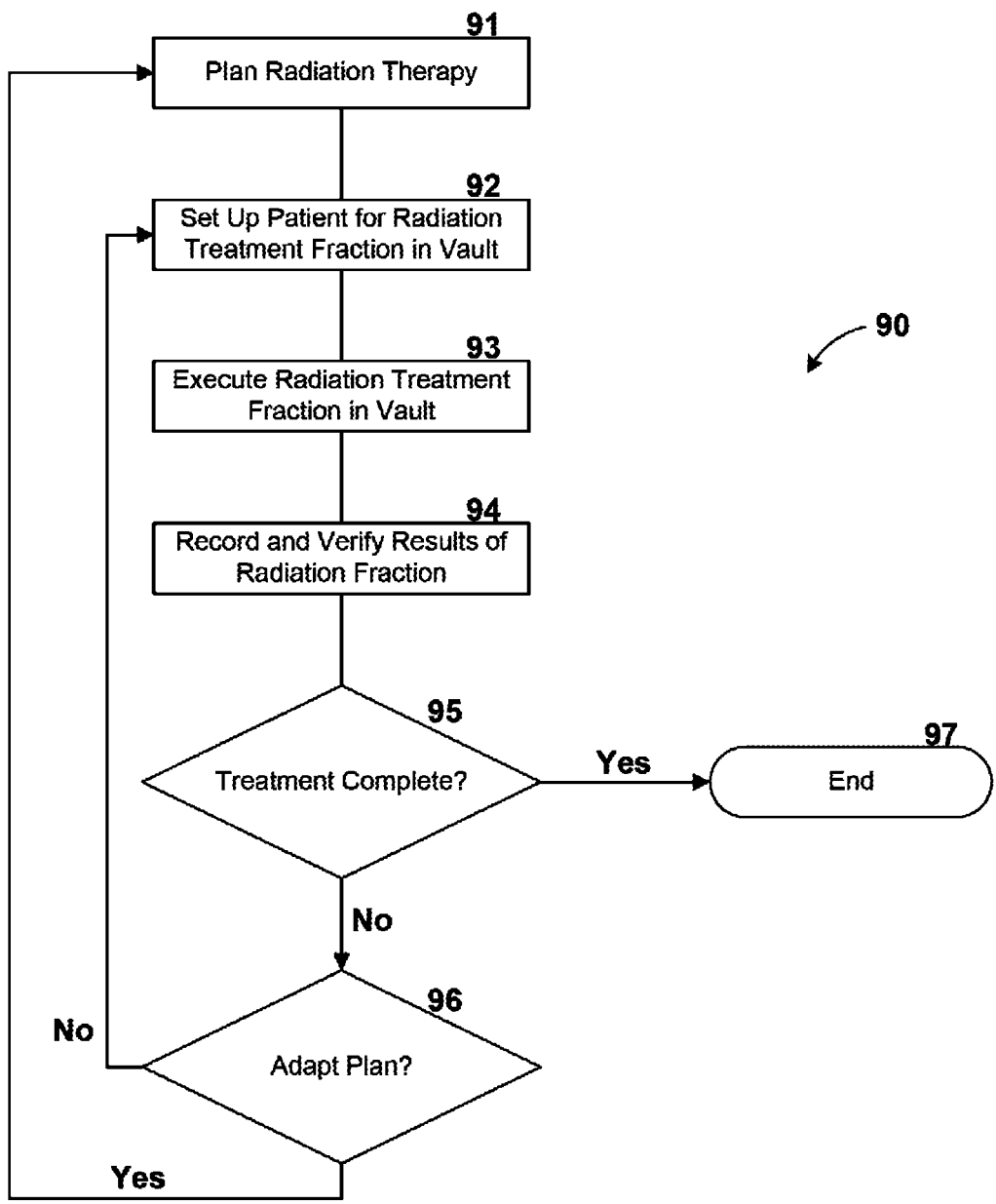
FIG. 2 is a flow diagram illustrating several aspects and uses of real time tracking to monitor the location and the status of the target as may occur in some embodiments.

FIG. 2 is a flow diagram illustrating several aspects and uses of real time tracking to monitor the location and the status of the target as may occur in some embodiments. In this embodiment, an integrated method 90 for radiation therapy includes a radiation planning procedure 91 that determines the plan for applying the radiation to the patient over a number of radiation fractions. The radiation planning procedure 91 may include an imaging stage in which images of a tumor or other types of targets are obtained using X-rays, CT, MRI, or ultrasound imaging. The images may be analyzed by a person to measure the relative distances between the markers and the relative position between the target and the markers. The coordinates of the tumor can be determined in a similar manner to ascertain the offset between the marker and the target.

The radiation planning procedure 91 can also include tracking the targets using the localization system 10 in an observation area separate from the imaging equipment. The markers 40 can be tracked to identify changes in the configuration (e.g., size/shape) of the target over time and to determine the trajectory of the target caused by movement of the target within the patient (e.g., simulation). For many treatment plans, the computer does not need to provide objective output data of the marker or target locations to a user in real time, but rather the data can be recorded in real time. Based on the images obtained during the imaging stage and the additional data obtained by tracking the markers using the localization system 10 in a simulation procedure, a treatment plan is developed for applying the radiation to the target.

The localization system 10 and the markers 40 enable an automated patient setup process for delivering the radiation. After developing a treatment plan, the method 90 includes a setup procedure 92 in which the patient is positioned on a movable support table so that the target and markers are generally adjacent to the sensor assembly. As described above, the excitation source is activated to energize the markers, and the sensors measure the strength of the signals from the markers. The computer controller may then (a) calculate objective values of the locations and/or orientations of the markers and the target relative to the machine isocenter, and (b) determine an objective offset value between the position of the target and the machine isocenter. The objective offset values can be provided to a user interface that displays the vertical, lateral and longitudinal offsets of the target relative to the machine isocenter. A user interface may, additionally or instead, display target rotation.

One aspect of several embodiments of the localization system 10 is that the objective values are provided to the user interface or other device by processing the position data from the field sensor 70 in the controller 80 or other computer without human interpretation of the data received by the field sensor 70. If the offset value is outside of an acceptable range, the computer automatically activates the control system of the support table to move the tabletop relative to the machine isocenter until the target isocenter is coincident with the machine isocenter. The computer controller generally provides the objective output data of the offset to the table control system in real time as defined above. For example, because the output is provided to the radiation delivery device, it can be with low periodicity (1-20 ms) and low latency (10-50 ms). If the output data is provided to a user interface in addition to or in lieu of the table controller, it can be with relatively higher periodicity (20-50 ms) and higher latency (50-200 ms).

In one embodiment, the computer controller also determines the position and orientation of the markers relative to the position and orientation of simulated markers. The locations of the simulated markers may be selected so that the target will be at the machine isocenter when the real markers are at the selected locations for the simulated markers. If the markers are not properly aligned and oriented with the simulated markers, the support table is adjusted as needed for proper marker alignment. This marker alignment properly positions the target along six dimensions, namely X, Y, Z, pitch, yaw, and roll. Accordingly, the patient is automatically positioned in the correct position and rotation relative to the machine isocenter for precise delivery of radiation therapy to the target.

Referring back to FIG. 2, the method 90 further includes a radiation session 93. An automated process may be used in which the localization system 10 tracks the target during the radiation session 93 and controls the radiation delivery device 20 according to the offset between target and the machine isocenter. For example, if the position of the target is outside of a permitted degree or range of displacement from the machine isocenter, the localization system 10 sends a signal to interrupt the delivery of the radiation or prevent initial activation of the beam. In another embodiment, the localization system 10 sends signals to automatically reposition a tabletop 27 and the patient 6 (e.g., as a unit) so that the target isocenter remains within a desired range of the machine isocenter during the radiation session 93 even if the target moves. In still another embodiment, the localization system 10 sends signals to activate the radiation only when the target is within a desired range of the machine isocenter (e.g., gated therapy). In the case of treating a target in the lung, one embodiment of gated therapy includes tracking the target during inspiration/expiration, having the patient hold his/her breath at the end of an inspiration/expiration cycle, and activating the beam 21 when the computer 80 determines that the objective offset value between the target and the machine isocenter is within a desired range. Accordingly, the localization system enables dynamic adjustment of the beam in real time while irradiating the patient. This is expected to ensure that the radiation is accurately delivered to the target without requiring a large margin around the target.

The localization system provides the objective data of the offset and/or rotation to the linear accelerator and/or the patient support table in real time as defined above. For example, as explained above with respect to automatically positioning the patent support table during the setup procedure 92, the localization system generally provides the objective output to the radiation delivery device at least substantially contemporaneously with obtaining the position data of the markers and/or at a sufficient frequency to track the target in real time. The objective output, for example, can be provided at a short periodicity (1-20 ms) and a low latency (10-20 ms) such that signals for controlling the beam 21 can be sent to the radiation delivery device 20 in the same time periods during a radiation session. In the case of terminating or activating the radiation beam, or adjusting the leaves of a beam collimator, it is generally desirable to maximize the refresh rate and minimize the latency. In some embodiments, therefore, the localization system may provide the objective output data of the target location and/or the marker locations at a periodicity of 10 ms or less and a latency of 10 ms or less.

The method 90 further includes a verification procedure 94 in which the real time objective output data from the radiation session 93 is compared to the status of the parameters of the radiation beam. For example, the target locations can be correlated with the beam intensity, beam position, and collimator configuration at corresponding time intervals during the radiation session 93. This correlation can be used to determine the dose of radiation delivered to discrete regions in and around the target. This information can also be used to determine the effects of radiation on certain areas of the target by noting changes in the target configuration or the target trajectory.

The method 90 can further include a first decision (Block 95) in which the data from the verification procedure 94 is analyzed to determine whether the treatment is complete. If the treatment is not complete, the method 90 further includes a second decision (Block 96) in which the results of the verification procedure are analyzed to determine whether the treatment plan should be revised to compensate for changes in the target. If revisions are necessary, the method can proceed with repeating the planning procedure 91. On the other hand, if the treatment plan is providing adequate results, the method 90 can proceed by repeating the setup procedure 92, radiation session 93, and verification procedure 94 in a subsequent fraction of the radiation therapy.

The localization system 10 provides several features, either individually or in combination with each other, that enhance the ability to accurately deliver high doses of radiation to targets within tight margins. For example, many embodiments of the localization system use leadless markers that are implanted in the patient so that they are substantially fixed with respect to the target. The markers accordingly move either directly with the target or in a relationship proportional to the movement of the target. As a result, internal movement of the target caused by respiration, organ filling, cardiac functions, or other factors can be identified and accurately tracked before, during and after medical procedures. Moreover, many aspects of the localization system 10 use a non-ionizing energy to track the leadless markers in an external, absolute reference frame in a manner that provides objective output. In general, the objective output is determined in a computer system without having a human interpret data (e.g., images) while the localization system 10 tracks the target and provides the objective output. This significantly reduces the latency between the time when the position of the marker is sensed and the objective output is provided to a device or a user. For example, this enables an objective output responsive to the location of the target to be provided at least substantially contemporaneously with collecting the position data of the marker. The system also effectively eliminates inter-user variability associated with subjective interpretation of data (e.g., images).

System Improvements Overview

Various of the disclosed embodiments propose improvements to achieve less than 100 ms gating latency. "Gating latency", as referred to herein, may include the elapsed time between motion of the target outside its pre-defined acceptable 'beam-on' volume to the time the therapy beam is terminated. As discussed above, the tumor location may be measured via model-based optimal estimation, using a set of internal fiducials whose motion is correlated with that of the tumor. The model may define a kinematic relationship between the set of tumor fiducials and the tumor itself. Given measured and assumed values of fiducial measurement noise and model input uncertainty, the filtering process may provide an optimal estimate of the tumor location.

Embodiments of the disclosed filtering process may allow for updating the estimated tumor location at the instant of each fiducial location measurement. This may be particularly useful in cases where the fiducial measurements occur in a serial rather than parallel fashion. Some embodiments support, e.g., setup, real-time tracking display, and gating for the prostate application. In the example radiation therapy applied to the prostate, e.g., the application may be generally characterized by slow-moving targets (<10 mm sec) exhibiting non-repetitive motion. Typical beam-hold latencies of 250-275 msec may be acceptable in this application.

An approximate breakdown of the system latency components for the Xycom 2® tracking station in three and two beacon/fiducial modes (3B/2B) may be found in FIG. 3. As indicated, the biggest improvements to latency may come from algorithmic improvements, but reductions in the other categories may be required as well to achieve latencies below 100 ms without using prediction (e.g., represented as negative algorithmic latency).

Various of the disclosed embodiments provide system performance improvements to support setup, real-time tracking display, real-time position streaming and gating, e.g., for tumor sites exhibiting respiratory motion. Real-time position streaming may appear as a Real Time Data Output (RTDO) to a user (e.g., target position and associated latency information). In some embodiments, the system may automatically assert a beam-hold to the Linear Accelerator (LINAC) based, e.g., on in-volume and latency criteria. If the treatment isocenter associated with the tumor (target) leaves a defined bounding-box region, or if the age of the computed target exceeds a defined threshold, the system may assert a beam-hold to the LINAC. This may "gate" the radiation beam and interrupt treatment. In some embodiments, the system will de-assert beam-hold to the LINAC only if both the in-volume and latency criteria are satisfied.

Respiratory motion may be characterized as semi-repetitive (12-20 breaths per minute) with significant displacement (typically 5-20 mm, though 40 mm may occur for respiratory motion) with correspondingly significant velocities (typically up to 30 mm/sec). Latencies under 100 ms may be achieved for RTDO using various filtering embodiments disclosed herein. An improved display update rate may also be provided for various of these applications.

Generally, there may exist a tradeoff between dynamic error (precision, tracking error) and latency. As latencies are driven shorter, the precision and tracking error may both degrade. Conversely, as the precision is improved the latencies may generally grow longer. As different signal outputs may serve different purposes, they may be optimized for this tradeoff independently. For example, the display outputs may be used for patient setup and need only have latencies necessary to support manual, interactive control of the patient table. The Beam-Hold signal, in contrast, may demand very short latencies in respiratory application where target motion is repetitive and velocities are high.

An improved system timing diagram contemplated in some embodiments may be found in FIGS. 4. 2B and 3B here refer to the number of inserted fiducials contemplated. By applying various of the disclosed embodiments to a system having the parameters of FIG. 4, considerably improved accuracy and treatment confidence may be achieved.

Figure 5:
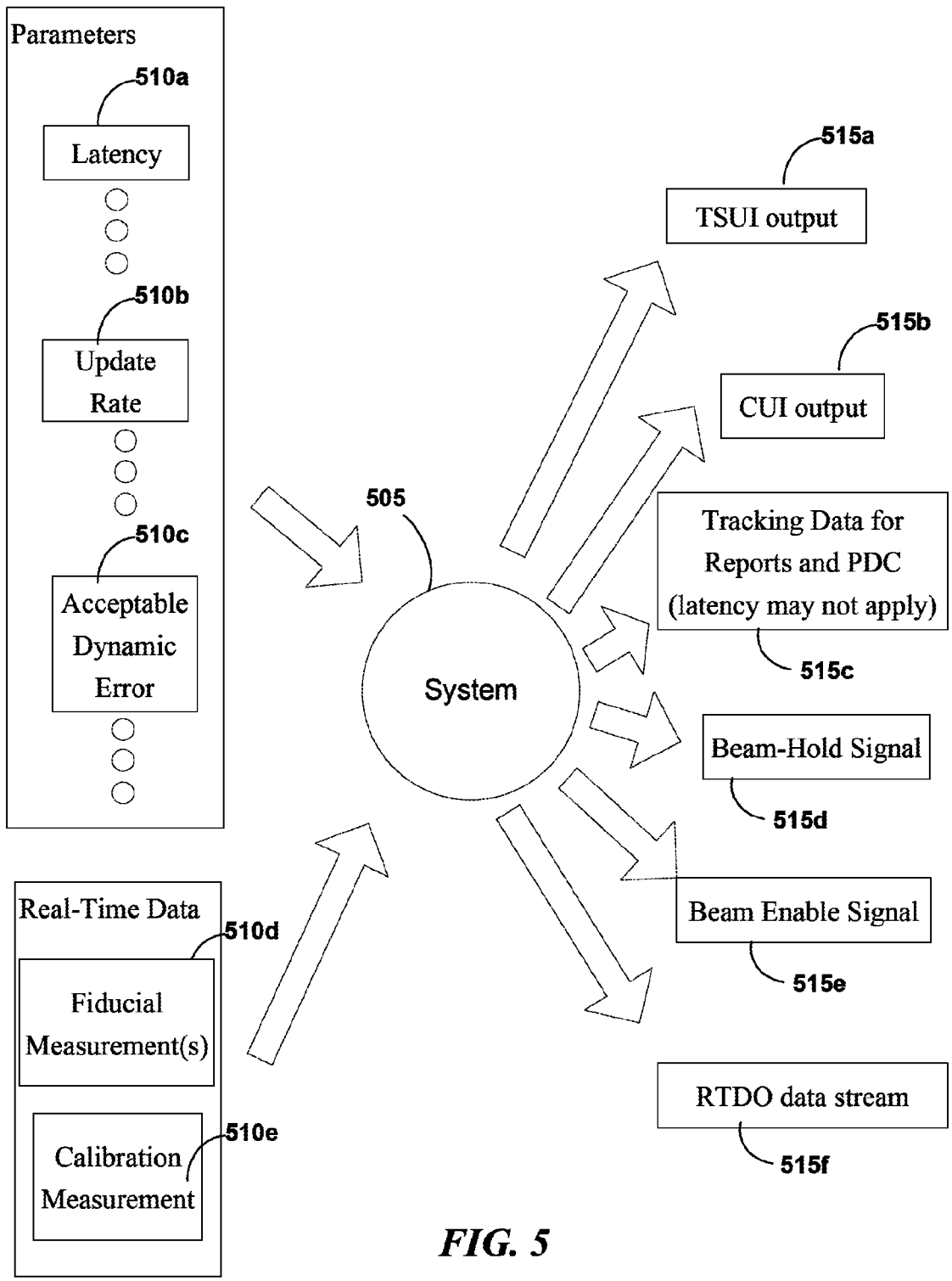
FIG. 5 is block diagram depicting inputs and outputs to a processing system considered in some embodiments.

Various of the disclosed embodiments provide six distinct signal outputs from a variety of inputs. FIG. 5 is block diagram depicting inputs 510a-e and outputs 515a-f to the system 505 considered in some embodiments. For example, a user or connected system may specify a desired latency 510a for one or more of the outputs, a desired update rate 510b for one or more of the outputs, and a desired acceptable dynamic error 510c for one or more outputs. The system may then generate the various outputs.

For example, some embodiments may provide a Tracking Station User Interface (TSUI) output 515a. The TSUI may be the user interface in the control room (i.e., outside of the treatment room), where users can monitor intra-treatment target motion and other system information.

Some embodiments may provide a Console User Interface (CUI) output 515b. The CUI may be the user interface in the treatment room where the user performs patient setup and motion monitoring prior to treatment.

Some embodiments may provide a Tracking Data for Reports and Patient Data Convert (PDC) outputs (latency may not be an applicable input in this instance) 515c. Reports allow for post-treatment summary and visualization of the therapy session. PDC may be used to convert stored patient session time history data into a form where it can be further analyzed. In some embodiments, latency may be informative, but not critical to usage.

Some embodiments may provide an Beam-Hold Signal 515d and a Beam-Enable Signal 515e.

Some embodiments may provide an RTDO data stream 515f. The RTDO signal may be used to control the location where therapy is delivered, such that treatment tracks target motion. The RTDO signal may also be used to control target location via couch motion, such that the target remains at a fixed location where treatment is being delivered. Hybrid use where both treatment beam tracking and couch tracking are utilized may also be used in some embodiments.

Real-time data inputs may include one or more fiducial measurements 510d and calibration measurements 510e. Fiducial measurements 510d may be acquired in serial as discussed herein. Calibration measurements 510e may be provided initially by an operator.

Improved Tracking System Component Overview

Figure 6:
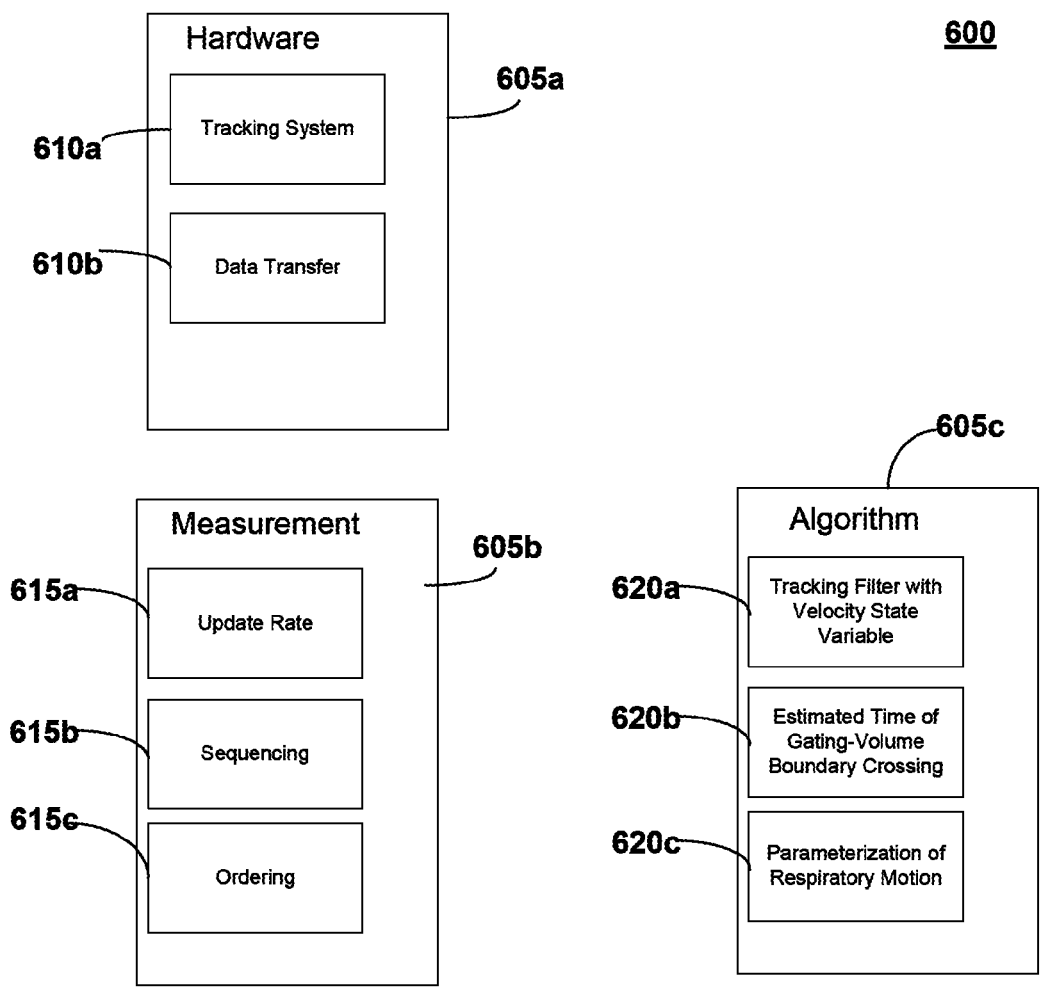
FIG. 6 is block diagram of various component improvements disclosed herein in some embodiments.

FIG. 6 is block diagram of various component improvements disclosed herein in some embodiments. Various embodiments contemplate latency improvements to support respiratory applications that include: Hardware technology upgrades (e.g., computational bandwidth and OS) 605a; Measurement improvements (e.g., higher update rates, new measurement sequences) 605b; and Algorithmic improvements (e.g., an improved tracking filter) 605c. In the system hardware 605a, various embodiments provide an improved tracking system 610a and an improved data transfer 610b system. In the system measurement components 605b, various embodiments provide an improved update rate component 615a, an improved sequencing component 615b, and an improved ordering component 615c. In the system software/firmware/hardware algorithms 605c, various embodiments provide an improved tracking filter with a velocity state variable 620a, an estimate time of gating-volume boundary crossing 620b, and an improved parameterization of respiratory motion 620c. The improvements identified in FIG. 6 are discussed in greater detail in the following sections and may be used (alone or in various combinations) to achieve sub 100 ms gating latency in one or more embodiments. For example, various of the improvements may be applied to achieve the features of the device considered in FIG. 4.

Algorithm—Serial Processing

Figure 7:
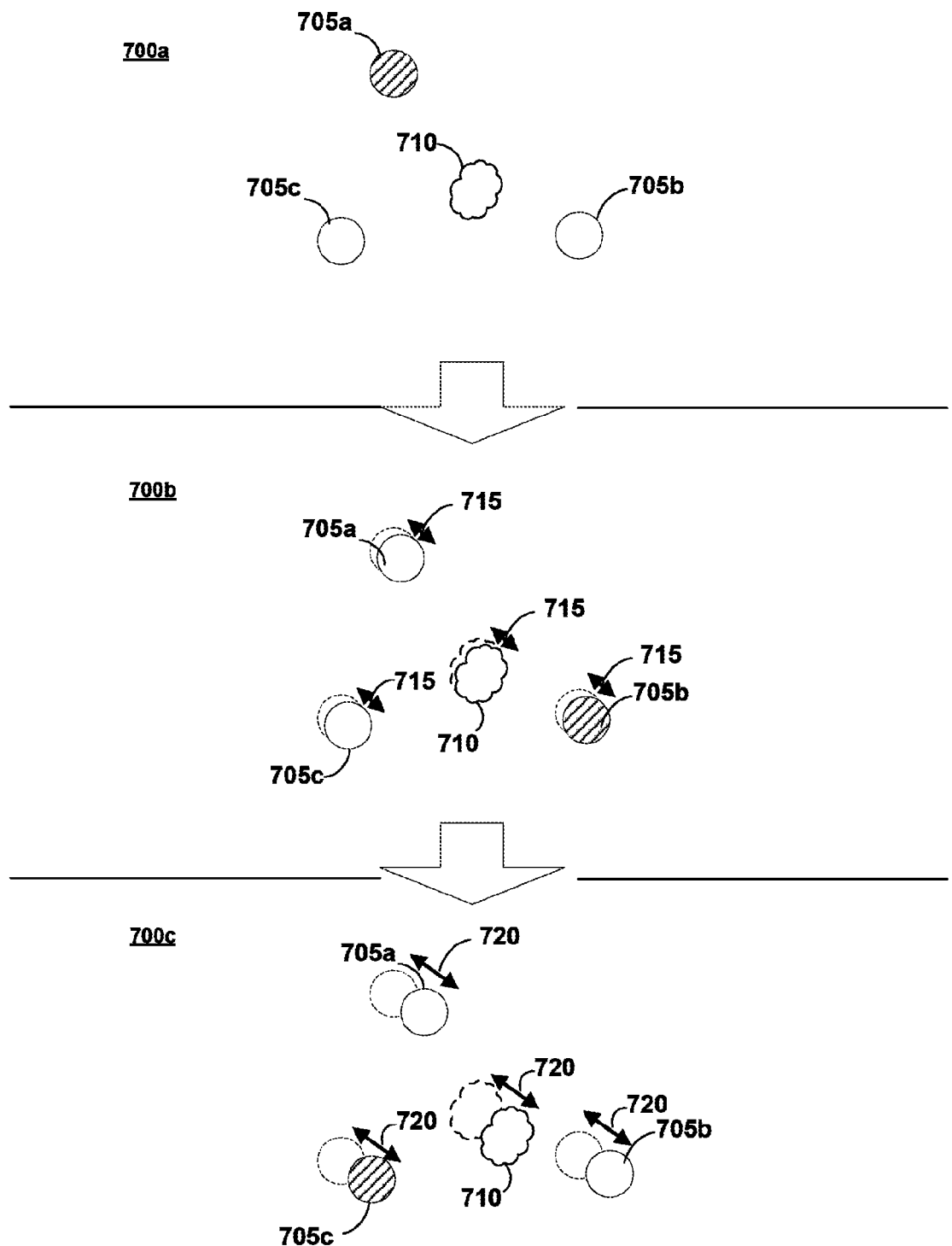
FIG. 7 is a series of time-lapse block diagrams depicting errors arising in serial fiducial measurements as may occur in some embodiments.

FIG. 7 is a series of time-lapse block diagrams depicting errors arising in serial fiducial measurements as may occur in some embodiments. At time 700a three fiducials 705a-c may be placed within the patient to monitor tumor 710. At time 700a the position of fiducial 705a may be determined (e.g., using radiofrequency measurements).

At time 700b, however, patient motion (e.g., respiratory motion) may translate the fiducials to a new position. For example, fiducial 705a may be translated a first offset 715. Though all three fiducials experience the same offset 715 in this example, one will recognize that in certain tissues different individual offsets may apply to each fiducial and/or to the target. Often, however, all the fiducials (and the tumor target 710) will experience the same offset, as depicted in this example.

At this time, the system may measure the position of fiducial 705b. Following another passage in time to time 700c, the fiducials may have translated to yet another set of positions. At this time, the system may measure the position of fiducial 705c. However, the existing measurement for fiducial 705a may be exceedingly stale as a substantial offset 720 may exist. In this example, the number of fiducials N is 3, but one will readily recognize embodiments where many more or fewer fiducials than three are used. As N increases the cumulative error between preceding fiducial positions and their current positions may increase dramatically.

Rather than rely upon past measured data, various embodiments update previous fiducial information (and may also update as-yet unacquired fiducial information) based upon newly acquired information. In this manner, the system may acquire a more accurate, holistic perspective of the fiducial positions. In some embodiments, these updates can be accomplished by employing a process model (e.g., a covariance process model) of the fiducial positions that is highly correlated. Correlated rigid body motion (translation/rotation) of fiducials may be accorded greater variance than the independent motion of the individual fiducials. With such a process model, the offset measurement attributable to target motion of a single fiducial, e.g., 705c, may be used to infer the offset 715, 720 applied to all three fiducials when updating the positions estimates.

Figure 8:
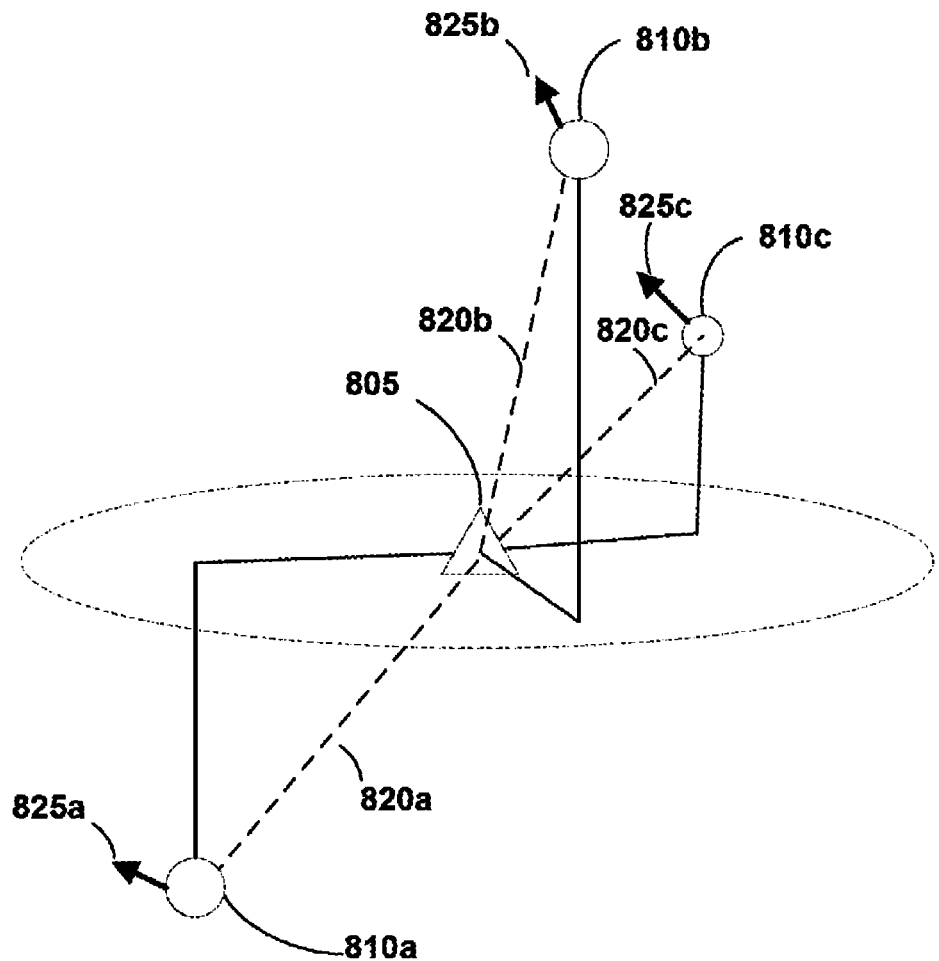
FIG. 8 is a three-dimensional depiction of centroid determination between serially measured fiducials as may occur in some embodiments.

FIG. 8 is a three-dimensional depiction of centroid determination between serially measured fiducials as may occur in some embodiments. Not only may successive offset errors affect the prediction of individual fiducial positions, but they may also affect inferred values. For example, one may wish to determine the three-dimensional position of a centroid 805 from measurements of fiducials 810a-c. Each error in the fiducial positions 820a-c will result in a corresponding offset from the true position of the centroid 805. Where the centroid 805 is being used to verify placement, to infer the fiducial group and/or tumor target velocity, etc. the consequences for this error may be dramatic. Accordingly, various embodiments contemplate inferring updated positions for the fiducials based upon their previous measurements and the currently measured fiducial position. A deformable tissue model, Bayesian predictor, or other model may be used to assist with the inference.

The tracking filter may use raw measurements of both fiducial position and orientation 825a-c to update its model, and to produce estimates of fiducial position and orientation. Orientation may not be used in some embodiments, but it may enhance estimator accuracy and precision. Fiducial orientation may be captured as a unit vector aligned with the longitudinal axis of the fiducial, where the sense of the vector is not known.

A Kalman filter model may be used to predict positions based on current position and fiducial centroid velocity. A low order model may be chosen for simplicity, sufficiency, and robustness. Some embodiments contemplate extending the Kalman filter model to capturing other linear system state-space representations. For example, the Kalman filter may be extended by: omitting the velocity state for largely stationary targets; adding rigid body angular velocity for significant rotational motion; including an acceleration state for highly irregular motion; adding internal state coupling to approximate tumor deformation dynamics; etc.

An extended Kalman Filter approach may be used for non-linear system models in some embodiments. A deformable tissue model may be incorporated into the Kalman or Extended Kalman filter design to improve accuracy. Particle Filters, Sequential Monte Carlo methods, and various Bayesian estimation methods may also be applied in some embodiments.

Algorithm—Serial Processing—Gating Volume Boundary

Figure 9:
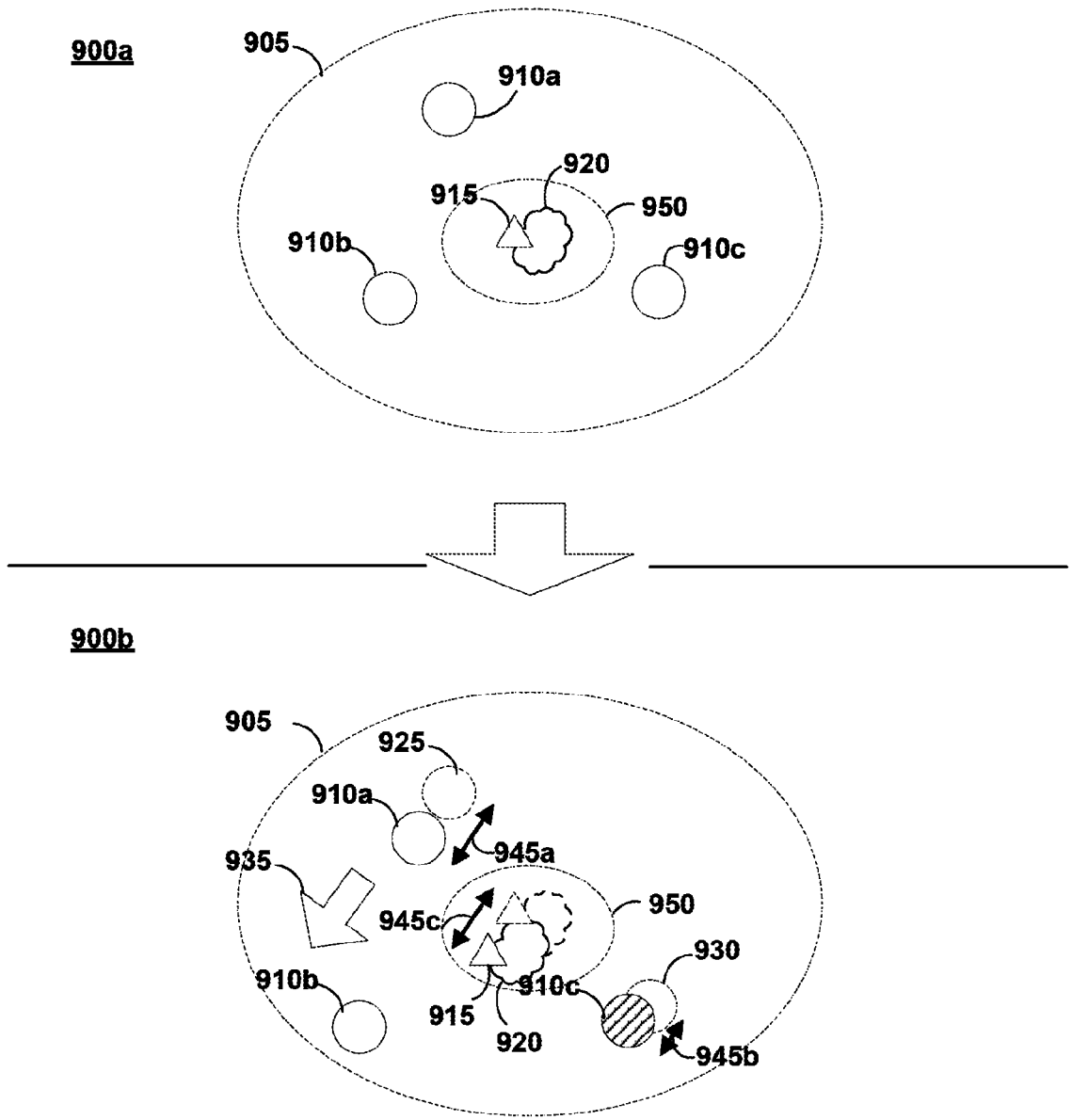
FIG. 9 a series of time-lapse block diagrams depicting predictive boundary gating-volume boundary intersection and velocity state variable as may occur in some embodiments.

FIG. 9 a series of time-lapse block diagrams depicting predictive boundary gating-volume boundary intersection and velocity state variables as may occur in some embodiments. At time 900a, fiducials 910a-c, are being used to monitor the position of tumor 920. At time 900a the fiducials 910a-c may be associated with a centroid 915 at a given position. For example, it may be ideal that the centroid 915 and tumor 920 overlap. Situations where the centroid and the tumor do not overlap may be accommodated by an assumed static offset (e.g., determined during patient planning). A region, referred to as a gating volume boundary 905/950 may serve as an outer threshold for treatment. For example, where destructive radiation therapy is being applied, it may be determined that applying the therapy outside the region 905 is harmful to the patient. In some embodiments, rather than representing the gating volume with respect to the individual fiducials, i.e. region 905, the gating volume may be referenced as a region 950 around the tumor/centroid. One will recognize additional variations, e.g., where individual boundaries are provided around each of the fiducials. Some embodiments may not even recognize a "target" and just focus upon one or more boundary gating volumes around the fiducials. In some embodiments, the fiducials may be centimeters apart, but the gating volume boundary may be only a few millimeters on a side around the tumor (e.g., the distance between the tumor and the boundary of region 950).

Accordingly, at time 900b the fiducials may begin moving in a direction 935 that takes them outside the region 905 (e.g., as a consequence of respiratory motion). At time 900b, the system may be measuring the position of fiducial 910c. Thus, while the system may not have explicitly measured the fiducial 910b to determine its dangerous proximity to the boundary 905, various embodiments contemplate the system inferring, e.g., the position of fiducial 910b and initiating appropriate action (e.g., disabling therapy, warning an operator, etc.). Again, one will readily recognize variations from this example. For example, the boundary assessment may be applied at the level of the computed target, and not at the constituent fiducial positions (e.g., the system may recognize that centroid 915 is approaching boundary 950, or that the target 920 at an offset from the centroid, is approaching boundary 950). Similarly, in some embodiments corrective action may only be taken after multiple fiducials traverse one or more boundaries.

Various embodiments contemplate several mechanisms by which fiducial and/or target and/or centroid velocity may be inferred to so as to preemptively identify breaches of a gating boundary, e.g., boundary 905/950. The computed velocity may be that of the fiducial centroid, and it may be an explicit state in a Kalman filter optimal estimator. The system may consider the centroid displacement 945c across measurements and/or the displacements 945a,b of previously measured fiducials as compared to their presently inferred position. In this manner, the system may consider the relative position (as measured or as inferred) of each fiducial, or the aggregate of the fiducials, to determine if the orientation is approaching an unsafe limit for treatment delivery. Although this example has separate displacements 945a-c for the fiducials and target, as discussed herein, the fiducials and target may share a same displacement in some embodiments.

If the target tracking filter were to computes a weighted centroid using the last valid position estimate for each fiducial, there would be a delay of one entire measurement to the target estimates. This approach may also introduce motion artifacts, as the prior samples may not have moved since they were last measured. These motion artifacts may present themselves as apparent deformation.

Partly to overcome these effects, some embodiments employ a target tracking filter having a semi-rigid body model feature and a centroid velocity modelling feature. With regard to the first feature, the new tracking filter may maintain a current rigid body model of the set of fiducials. This permits updates to the centroid (and target) with each new measurement without incurring the delay associated with integrating over the last three measurements. In order to maintain a current rigid body model, the tracking filter may measure and account for changes in rotation and deformation over the course of the tracking session. The rigid body model may consist of: correlated process noise associated with rigid body translation and rotation (generalized force and moment disturbances on a rigid body); and an estimated centroid velocity element in the state vector used in the time-update of the estimated fiducial location.

With regard to the centroid velocity modelling feature, the target tracking filter may also estimate centroid velocity (in addition to centroid position). Incorporating velocity into the signal model may allow the use of several previous measurements in addition to the most current measurement in arriving at low-latency, low-variance target position estimates. In this manner, targets with high velocities (10-30 mm/sec or more) may still be tracked with minimal latency.

Some embodiments may not incorporate velocity into the filter model. Velocity may be used to improve the predictive element of estimation, and thereby decrease estimator error, particularly with high velocities. In this manner, targets with high velocities (10-30 mm/sec or more) may still be tracked with high precision and minimal latency.

The new target tracking filter may also compute position (and velocity) estimates for each of several lag times. A medium-latency, low-variance estimate may be utilized for UI display, beam-enable and reporting purposes. A low-latency estimate (at the expense of degraded variance) may be utilized for the beam-hold signal (e.g., the treatment applied within boundary 905/950). The low latency estimate may generate the position that will first exit a defined treatment volume. The medium latency estimate may be the last to re-enter the volume.

Some embodiments employ the latency-optimized and/or the variance-optimized signal for real-time output. If the subscriber of the data were known to be using prediction in a respiratory motion application, the variance-optimized version of the signal may be most suitable in some instances. Conversely, if no prediction were used by the subscriber in a respiratory application, the latency-optimized solution may be desired. Note that the real-time output may not appear to the clinician, but may be used internally for assessment purposes in some embodiments.

A secondary in-volume/out-of-volume determination may use the variance-optimized target position estimate (the same position estimate used for displays and reports) with no separate estimate of boundary crossing time. A "secondary in-volume/out-of-volume" determination as referred to herein is an independent volume assessment performed for system safety reasons. The secondary in-volume assessment is an independent assessment using the same inputs as were used for a primary in-volume assessment. The secondary assessment provides a safety function. Some embodiments select a secondary assessment which nominally produces results numerically identical to the primary assessment, in which case a discrepancy between the two would indicate a fault. In some embodiments, the secondary assessment may be designed to be approximately equivalent to the primary assessment, with a corresponding definition of allowed deviations. Exceeding the deviations may be construed as a fault. In either case, the primary in-volume assessment may be an input to the primary channel gating signal and the secondary in-volume assessment may be an input to the secondary channel gating signal.

This approach may provide 'symmetric' beam enable/disable latencies on each of the primary and secondary relay control channels, though the beam-hold signal as seen by the LINAC (with primary and secondary relays in series) may be very low-latency (e.g. 50 ms mean) and the beam-enable may be of greater latency (e.g. 150 ms mean).

For safety reasons, the DGI may utilize redundant sets of relays to facilitate the beam-hold gating function. The primary relays used for gating may be driven by a primary in-volume and primary target age (time since measurement) determination. The secondary relays for gating may be driven by alternative in-volume and alternative target age determinations.

A relay control may be used to provide a single in-volume/out-of-volume determination per measurement at some desired look-ahead or lag time. In some embodiments, there are generally two advantages to providing an estimated crossing time over the snapshot. First, the estimated crossing time may help reduce the temporal variance jitter of the beam-hold signal by eliminating the temporal quantization associated with discrete position updates. Second, the DGI can still autonomously open the primary relay in a timely manner even on those occasions when position updates are delayed or dropped due to operating system or communication issues.

Algorithm—Serial Processing—Process Flow

Figure 10:
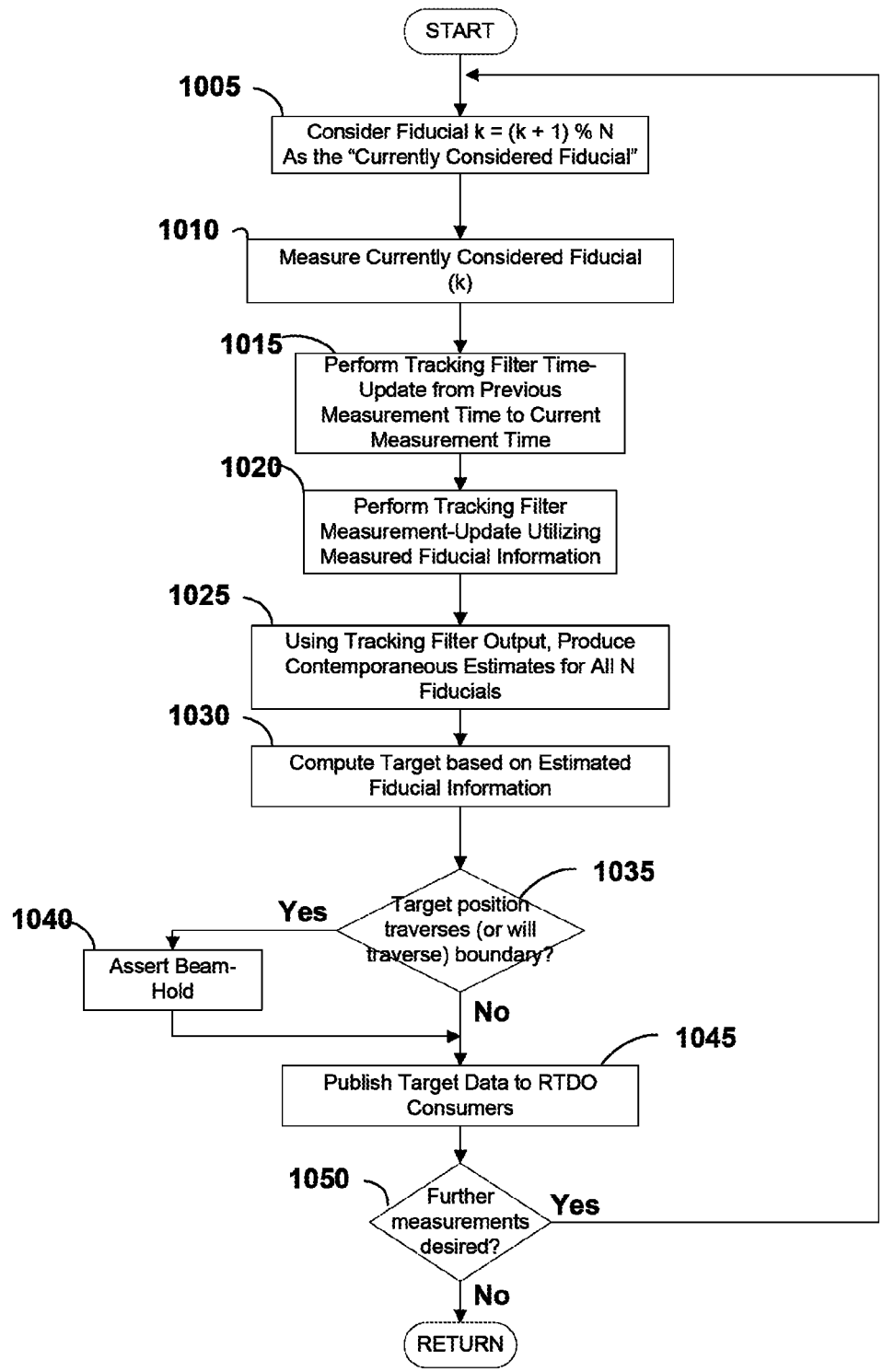
FIG. 10 is a flow diagram generally depicting process steps that may occur during an improved serial fiducial assessment process as may occur in some embodiments.

FIG. 10 is a flow diagram generally depicting process steps that may occur during an improved serial fiducial assessment process using an improved filter as may occur in some embodiments. It may be desirable to predict the positions of all fiducials at the time of the newly acquired measurement datum—this may include a prediction of the measurement corresponding to the currently measured fiducial. Estimating all fiducials may make the best use of the available information in the measured fiducial data. For example, if a particular fiducial measurement had an unusually large associated measurement noise, the current estimate for the fiducial might rely more heavily on the predictive model than on the measurement itself.

Accordingly, a Kalman filter update and/or Bayesian update using a tissue model may be applied to each of the other fiducials to generate an estimated fiducial position. This estimate may be produced contemporaneously for all fiducials, and may be a higher fidelity measure of the fiducial position than the raw measurement itself.

At block 1005, the system may consider the next of the N fiducials (e.g., with zero-based indexing, the system may consider the $k^{th}$ fiducial where k=(k+1)% N). At block 1010, the system may measure the currently considered fiducial's position and/or orientation. In some embodiments, as each fiducial is measured, the filter may be updated with the measurement (time update and measurement update), and a new estimate for all fiducials may be produced. For use in gating and RTDO, this may be a contemporaneous estimate of all fiducials. This estimate of all the fiducials may be 80 ms prior to the current measurement, e.g., applied at a user interface. Thus the filter may be updated in a round-robin fashion, with each filter update producing an estimate for all N fiducials.

At block 1015, the system may perform a tracking filter "time update" prediction from the previous measurement time to the current measurement time. For example, in a Kalman filter the system may increment the timestep and propagate the state estimates and estimator covariance from the previous measurement time to the current measurement time. This propagation in time may make use of the Kalman filter state-transition matrix element relating the past state vector to the current state vector. The propagation may also make use of known forcing inputs using the Kalman filter control input distribution matrix. This state propagation approach, based on prior states and forcing inputs, may also be used with extended Kalman filters, as discussed herein, in some embodiments.

At block 1020, the system may perform a tracking filter "measurement update" using the measured information for the currently considered fiducial. This may correspond to the measurement update (correction) step in a Kalman filter operation. This measurement update step may correct the predicted state estimates using the measured data in conjunction with the Kalman feedback gain matrix. In some instances this may be a full, time-varying feedback gain matrix. In other instances, this may be a computed steady-state feedback gain matrix. The measurement update to the Kalman filter may utilize real-time measured sensor covariance to update the Kalman filter estimator error covariance matrices, or it may utilize a fixed, stationary representation of the measurement covariance.

At block 1025, the system may produce contemporaneous estimates for all N fiducials. In a Kalman filter, this may correspond to the comparison of the predicted values with the measured value of the currently considered fiducial to generate a plurality of output estimates for the N fiducials.

At block 1030, the system may determine the target position, e.g., the centroid of the contemporaneous fiducial estimates of block 1025.

At block 1035, the system may consider if any of the fiducials (or the centroid, or the target, depending upon the embodiment) reflect a potentially dangerous boundary traversal. As discussed, this may be accomplished by considering the motion of the fiducials individually or in the aggregate via a centroid. As discussed elsewhere herein, the system need not wait for the fiducial, centroid, or target to actually cross the boundary before raising the alarm, but may infer the crossing from the fiducials' currently predicted trajectories. Target position, rather than fiducial position, may be used for treatment beam gating, and may be the output published to RTDO consumers in some embodiments.

Where such a crossing seems imminent, at block 1040 the system may raise an alarm and/or assert a beam-hold (e.g., to cease treatment). The "alarm" that is raised may not really be an auditory alarm, but rather a beam-hold assertion to the LINAC.

At block 1045, the system may publish the results to the various outputs. A smooth, less granular target estimated position may be determined for medium latency displays (TSUI and CUI), while a granular, unsmoothed target may be reported to low latency displays, e.g., the RTDO data stream.

For the primary in volume/out-of-volume determination in a respiratory application, the tracking station may also send the timestamp at which boundary crossing is expected. The DGI may change the primary relay state at the scheduled time, in much the same way that the DGI currently opens the primary relay at a predefined age timeout.

At block 1050, the system may consider if additional measurement cycles are to be performed. If so, the process may be performed with the next of the serially considered fiducials.

As mentioned in herein, in some embodiments the boundary crossing applies to the computed target/centroid position rather than to the individual fiducial positions. A target position may be computed using noise-weighted fiducial estimates and the isocenter offset from centroid defined in the Patient Plan. The estimator velocity state may be the estimated velocity of the fiducial centroid, and thus the estimated velocity of the target. The beam hold may be applied either when the target is exiting the region, or when the measurement data has become too stale. The target age may be determined to be stale and a beam hold applied when the low latency measurement is greater than the minimum of the time to boundary crossing and a maximum allowed target position measurement age (as inferred from the fiducials).

A target position and/or orientation may be computed at each measurement time based on the corresponding set of fiducial estimates. This target computation may be performed by calculating a weighted average offset of the fiducials from an initial state, and additively applying this average offset to the initial state target position/orientation to produce the current target. Weights may be derived based upon tracking filter covariance data as discussed herein. Weights may also be derived based upon tracking filter covariance data to preferably consider fiducials with lower estimator variance, and de-weight fiducials with higher estimator variance.

The initial state target position/orientation computation may utilize a large number of measurements to provide enhanced mitigation of noise-induced errors. Leveraging estimator derived weights, this computation may determine the positional centroid of the aggregate accumulated fiducial measurements, apply a treatment isocenter offset defined in the patient plan to this centroid, and thereby produce the initial target position. An initial target orientation may be determined using a weighted, rigid, Procrustes fit of the averaged fiducials to the corresponding planned fiducials.

Example Measurement Sequence Timings

Figure 11:
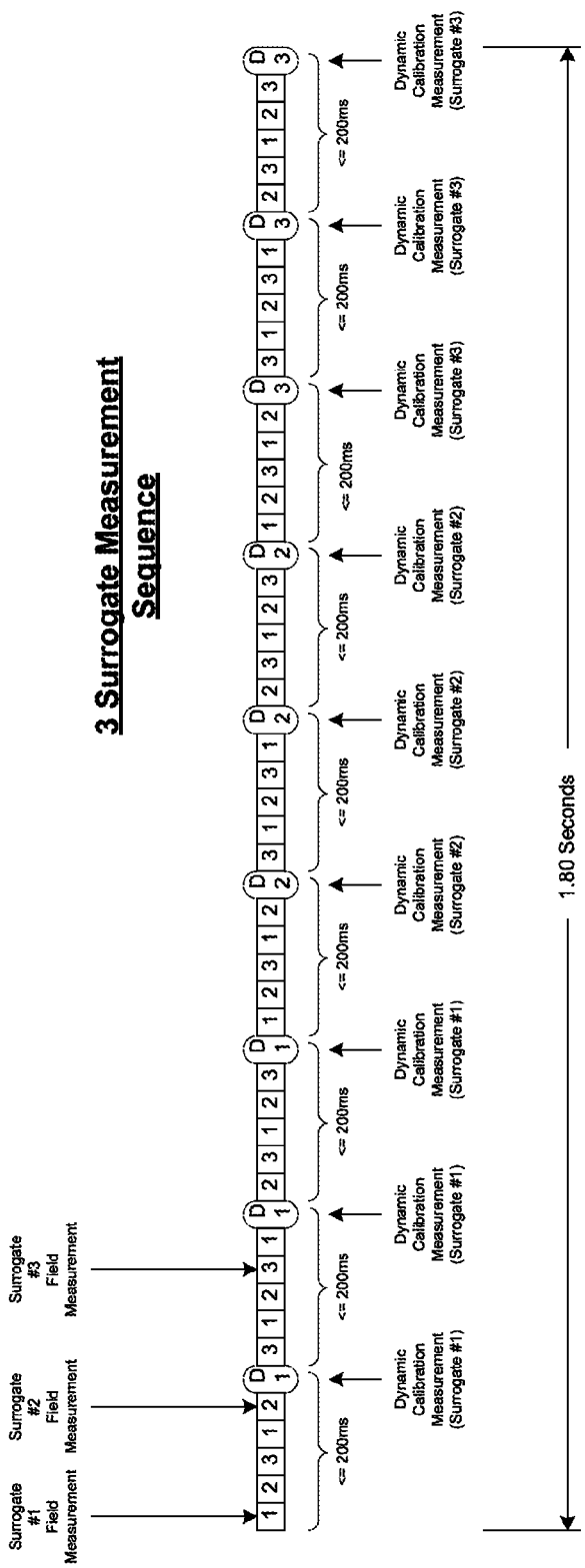
FIG. 11 is timing diagram for an example series of three fiducial measurements as may be taken in some embodiments.
Figure 12:
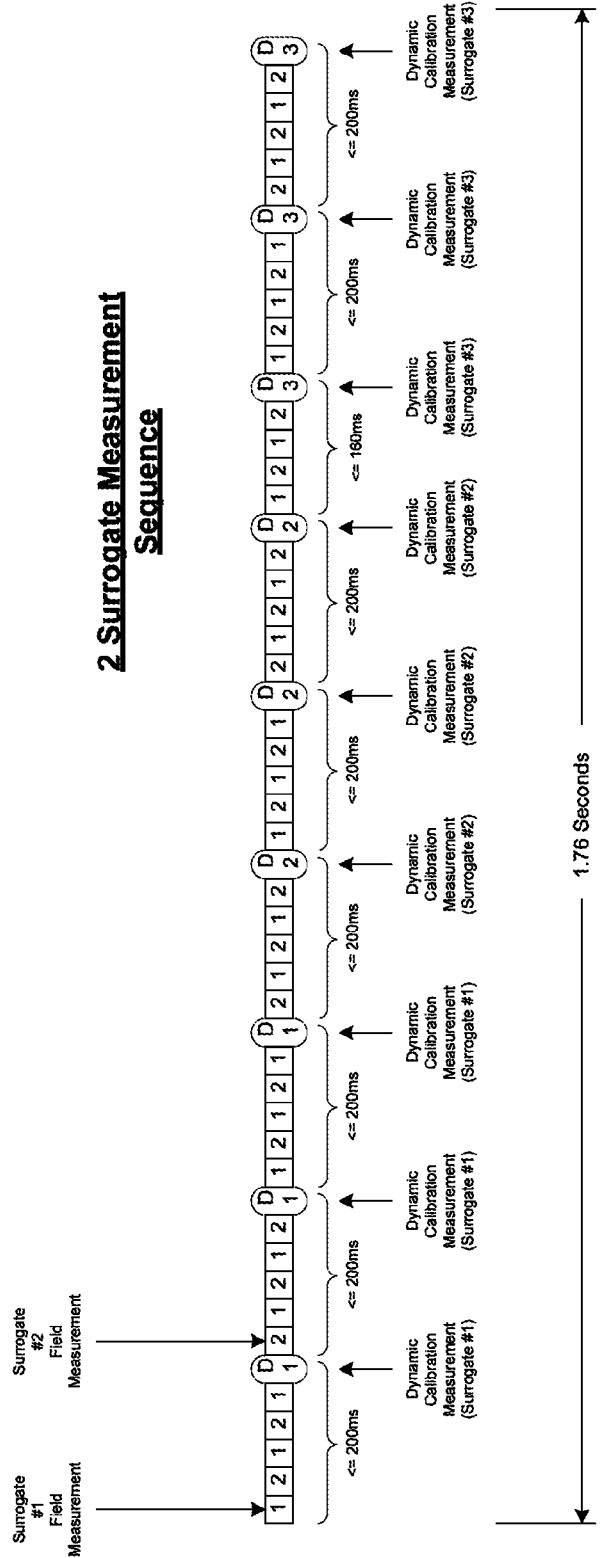
FIG. 12 is timing diagram for an example series of two fiducial measurements as may be taken in some embodiments.
Figure 13:
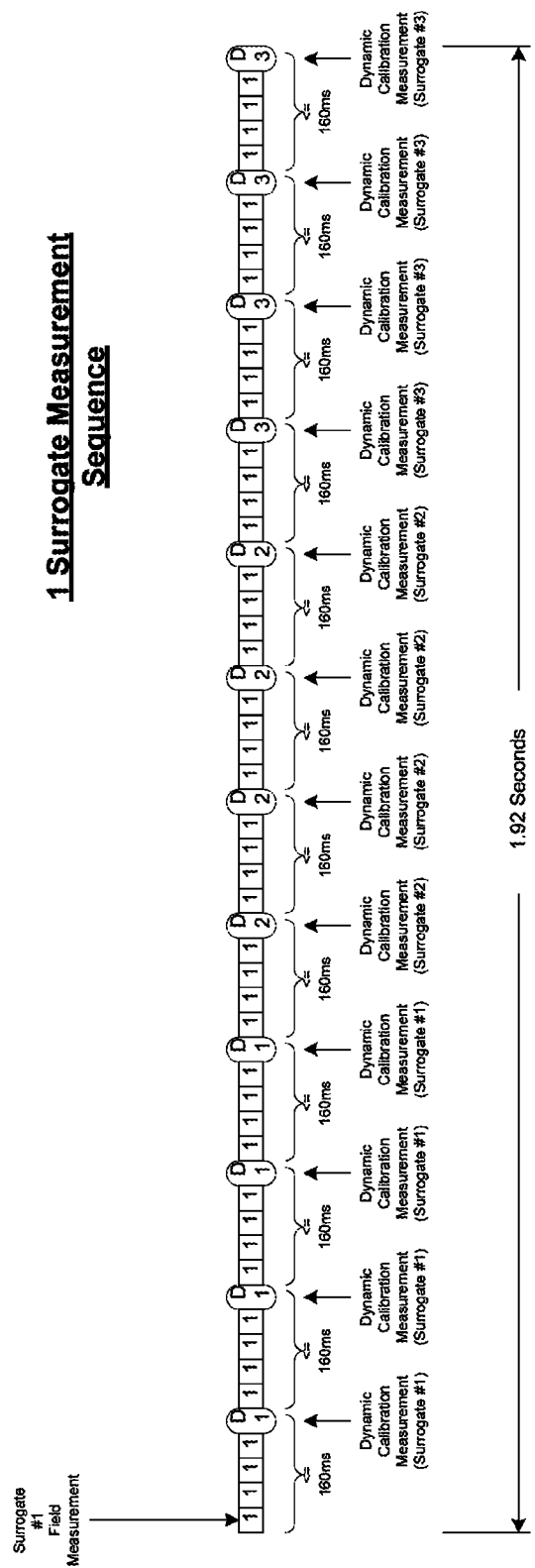
FIG. 13 is timing diagram for an example series of single fiducial measurements as may be taken in some embodiments.

FIG. 11 is timing diagram for an example series of three fiducial measurements as may be taken in some embodiments. FIG. 12 is timing diagram for an example series of two fiducial measurements as may be taken in some embodiments. FIG. 13 is timing diagram for an example series of single fiducial measurements as may be taken in some embodiments. As indicated, dynamic calibration measurements may be performed for each of the three fiducials, even when field measurements for only one or two fiducials are made.

The dynamic calibration measurements may still be made at the center frequencies of all 3 fiducials even if actual field measurements from just one or two fiducials are being taken.

The dynamic calibration measurements may be used to determine a transfer function based on the flux at the array coils during digitization. The transfer function may be used to identify crosstalk between the channels. As indicated, the transfer function may be performed on a frequency-by-frequency basis (e.g., for each frequency associated with a distinct fiducial).

The dynamic calibration measurements may also mitigate the effect of the LINAC gantry on localization accuracy. For example, where the LINAC gantry metal distorts the fiducial's field resulting in a loss of accuracy when the gantry is to the side or overhead. The dynamic calibration process may measure the mutual inductance between all the coils in the array. The mutual inductance may be used to estimate the effect the gantry metal has on the fiducial field measurements and to apply a correction to estimate what the 'free-space' (no gantry metal) measurements would have been.

The mutual inductance and the correction factors applied may be frequency-independent. A more robust estimate of the mutual inductance may be achieved if measurements are taken at multiple frequencies and a weighted average of the mutual inductance determined (e.g., where the weighting is inversely proportional to the variance of the single-frequency measurements).

Hardware—Tracking System

As shown in FIG. 3, the example tracking station exhibits 38 ms average processing time. This time reflects the time between the front-end reception of data and the publishing of new target positions at the DGI.

A portion of the 38 ms may comprise actual localization and target computation. Another portion of the average processing time is a "waiting time". During the "waiting time" the received front-end data may wait for the OS scheduler to start work on the localization task. The "wait time" may also include time the system is interrupted by the scheduler to work on other tasks. Some embodiments contemplate hardware platforms having between 4 and 8 processors. A goal of 10 msec mean processing time may be set for some embodiments. For example, FIG. 4 depicts a 13 ms processing time.

Hardware—Data Transfer

As shown in FIG. 3, the example tracking station exhibits a mean data transfer time of 20 msec. This time may reflect the difference between the end of a front-end measurement to receipt of data at the tracking station.

Data transfer improvements may include: reading each superinterval out of an FPGA as it completes rather than waiting until the end of the entire measurement; optimizing software buffering on the front-end; employing a UDP transfer protocol from the front-end to the tracking station. A "super-interval" is a group of subintervals over which the measurement results are averaged. UDP may be used for fiducial measurements and inter-leaved dynamic calibration measurements as well as for synchronous dispatch of estimated fiducial positions and estimated target positions. These improvements may be exploited to improve the data transfer time without printed circuit board changes to the front end in some embodiments.

Measurement—Update Rate

In some embodiments, there is an effective delay associated with the measurement process equal to half the integration time of the measurement (for uniform excitation). Half the integration time in some embodiments may be roughly 40 ms. This can be reduced to 20 ms by doubling the measurement update rate to 20 Hz or to 16 ms with a 25 Hz measurement update rate.

Measurement—Sequencing

Measurement sequencing of many prior art systems exhibits relatively large, irregular gaps between transponder measurements during which array calibration is executed. In addition, prior art measurement sequencing for two transponder plans may use the same measurement sequencing as three-transponder plans resulting in additional measurement gaps during measurement of the disabled (or not present) transponder. These gaps in measurement degrade the precision and latency of the target estimates.

Some embodiments use measurement sequences which provide much smaller, more regular gaps in fiducial measurements for array calibration, and which do not spend time measuring disabled fiducials.

Measurement—Ordering

The magnetic localization subsystem may employ excitation diversity to mitigate the effect of coherent interference. For example, certain super-intervals of the measurement may contribute much more signal energy than others. The effective time of a given measurement may not be half-way through the duration of the measurement as would be the case with uniform excitation (identical excitation superintervals). There is an inherent latency in the measurement process equal to the effective time of the measurement until the end of the measurement when the data is available to process.

This contribution to the latency may be minimized by placing the superintervals in order of increasing signal energy across the measurement. The effective time of the measurement may be computed from the right-singular-vector of the SVD of the measurement.

Algorithm—Parameterization of Respiratory Motion

Knowledge of the expected motion to be tracked may provide improved tracking performance (precision, latency). Parameterization of the target tracking filter for a worst case motion may lead to excessive estimate variance for typical motion. Parameterization for worst case motion may assume a model that by definition is not typical, and accordingly compromises typical performance in terms of estimator variance. For example, assuming particularly high values for certain process noise elements may result in elevated Kalman filter gains and hence more sensitivity to measurement noise.

Parameterization of the filter for typical motion may lead to excessive latency, and/or tracking error for worst case motion. Parameterization of the tracking filter can be accomplished in, e.g., three ways: Preset parameterization; Examination of the observed motion during LI/LC (session test); Examination of the most recently observed motion (e.g., last 5-10 seconds) throughout tracking.

Preset parameterizations for general classes of patient tumor motion (e.g., (a) slow, shallow, regular breather, (b) irregular, high-amplitude breather, etc.) may be prepared in some embodiments. These parameterization may comprise associated quality metric thresholds and process noise parameters for each preset.

In some embodiments, the Kalman filter dynamic model may be selected based on observed motion. The order of the Kalman filter estimator could be increased/decreased based upon observed motion (some motion profiles may benefit from augmenting the Kalman filter state vector with an acceleration state). Some embodiments may switch between a linear or non-linear estimator model based on which provides better performance.

Computer System

Figure 14:
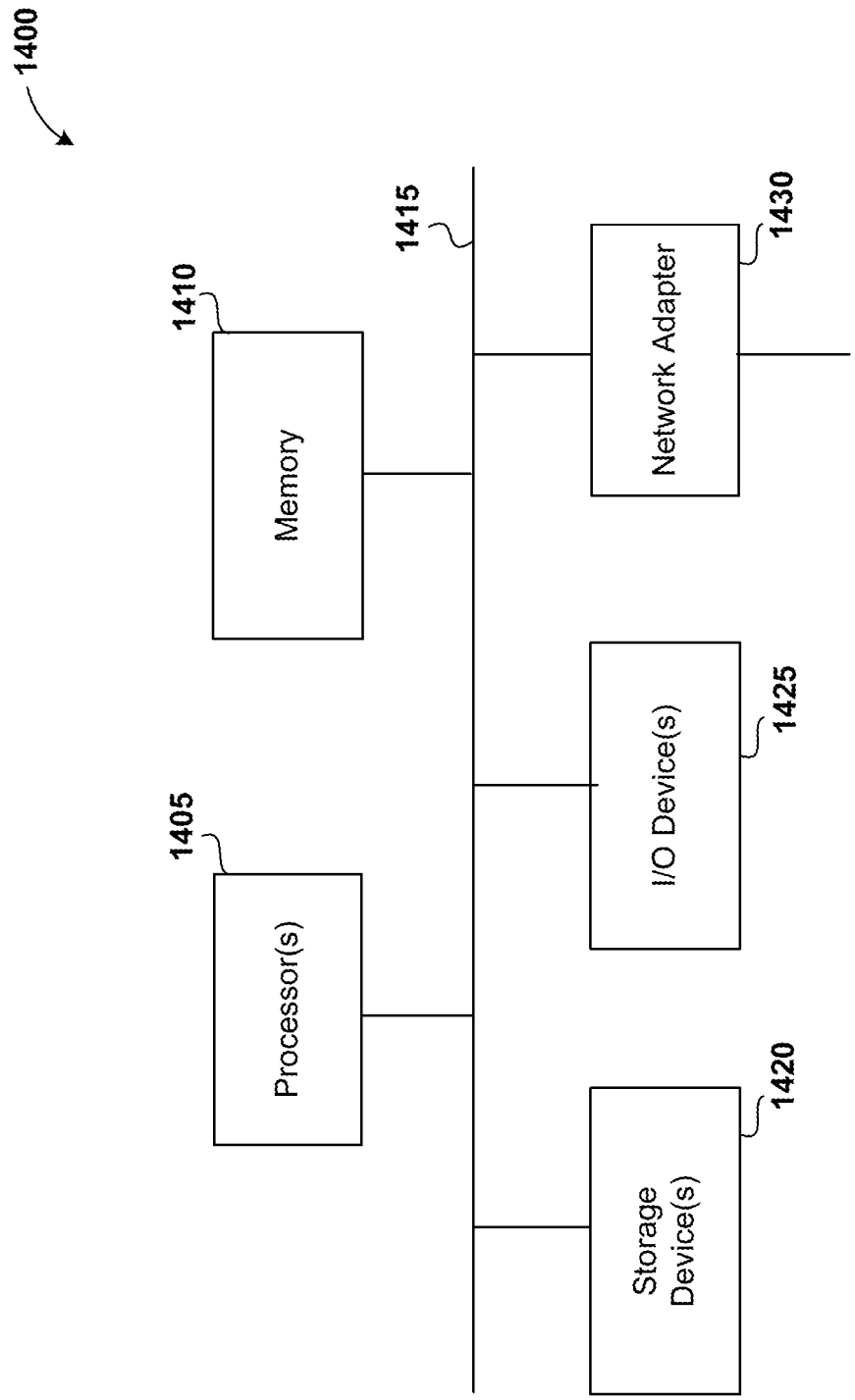
FIG. 14 is a block diagram of a computer system as may be used to implement features of some of the embodiments.

FIG. 14 is a block diagram of a computer system as may be used to implement features of some of the embodiments. The computing system 1400 may include one or more central processing units ("processors") 1405, memory 1410, input/output devices 1425 (e.g., keyboard and pointing devices, display devices), storage devices 1420 (e.g., disk drives), and network adapters 1430 (e.g., network interfaces) that are connected to an interconnect 1415. The interconnect 1415 is illustrated as an abstraction that represents any one or more separate physical buses, point to point connections, or both connected by appropriate bridges, adapters, or controllers. The interconnect 1415, therefore, may include, for example, a system bus, a Peripheral Component Interconnect (PCI) bus or PCI-Express bus, a HyperTransport or industry standard architecture (ISA) bus, a small computer system interface (SCSI) bus, a universal serial bus (USB), IIC (I2C) bus, or an Institute of Electrical and Electronics Engineers (IEEE) standard 1394 bus, also called "Firewire".

The memory 1410 and storage devices 1420 are computer-readable storage media that may store instructions that implement at least portions of the various embodiments. In addition, the data structures and message structures may be stored or transmitted via a data transmission medium, such as a signal on a communications link. Various communications links may be used, such as the Internet, a local area network, a wide area network, or a point-to-point dial-up connection. Thus, computer readable media can include computer-readable storage media (e.g., "non transitory" media) and computer-readable transmission media.

The instructions stored in memory 1410 can be implemented as software and/or firmware to program the processor(s) 1405 to carry out actions described above. In some embodiments, such software or firmware may be initially provided to the processing system 1400 by downloading it from a remote system through the computing system 1400 (e.g., via network adapter 1430).

The various embodiments introduced herein can be implemented by, for example, programmable circuitry (e.g., one or more microprocessors) programmed with software and/or firmware, or entirely in special-purpose hardwired (non-programmable) circuitry, or in a combination of such forms. Special-purpose hardwired circuitry may be in the form of, for example, one or more ASICs, PLDs, FPGAs, etc.

Remarks

The above description and drawings are illustrative and are not to be construed as limiting. Numerous specific details are described to provide a thorough understanding of the disclosure. However, in certain instances, well-known details are not described in order to avoid obscuring the description. Further, various modifications may be made without deviating from the scope of the embodiments. Accordingly, the embodiments are not limited except as by the appended claims.

Reference in this specification to "one embodiment" or "an embodiment" means that a particular feature, structure, or characteristic described in connection with the embodiment is included in at least one embodiment of the disclosure. The appearances of the phrase "in one embodiment" in various places in the specification are not necessarily all referring to the same embodiment, nor are separate or alternative embodiments mutually exclusive of other embodiments. Moreover, various features are described which may be exhibited by some embodiments and not by others. Similarly, various requirements are described which may be requirements for some embodiments but not for other embodiments.

The terms used in this specification generally have their ordinary meanings in the art, within the context of the disclosure, and in the specific context where each term is used. Certain terms that are used to describe the disclosure are discussed below, or elsewhere in the specification, to provide additional guidance to the practitioner regarding the description of the disclosure. For convenience, certain terms may be highlighted, for example using italics and/or quotation marks. The use of highlighting has no influence on the scope and meaning of a term; the scope and meaning of a term is the same, in the same context, whether or not it is highlighted. It will be appreciated that the same thing can be said in more than one way. One will recognize that "memory" is one form of a "storage" and that the terms may on occasion be used interchangeably.

Consequently, alternative language and synonyms may be used for any one or more of the terms discussed herein, nor is any special significance to be placed upon whether or not a term is elaborated or discussed herein. Synonyms for certain terms are provided. A recital of one or more synonyms does not exclude the use of other synonyms. The use of examples anywhere in this specification including examples of any term discussed herein is illustrative only, and is not intended to further limit the scope and meaning of the disclosure or of any exemplified term. Likewise, the disclosure is not limited to various embodiments given in this specification.

Without intent to further limit the scope of the disclosure, examples of instruments, apparatus, methods and their related results according to the embodiments of the present disclosure are given below. Note that titles or subtitles may be used in the examples for convenience of a reader, which in no way should limit the scope of the disclosure. Unless otherwise defined, all technical and scientific terms used herein have the same meaning as commonly understood by one of ordinary skill in the art to which this disclosure pertains. In the case of conflict, the present document, including definitions will control.

What is claimed is:

1. A computer-implemented method, comprising:
   determining a first position of a first fiducial of a plurality of fiducials, the plurality of fiducials located in or on a portion of a human body, the plurality of fiducials each associated with a plurality of preliminary positions;
   predicting a first plurality of positions associated with the plurality of fiducials based upon the determined position of the first fiducial and the plurality of preliminary positions;
   determining a first target position based upon the first plurality of positions;
   determining a second position of a second fiducial of the plurality of fiducials;
   predicting a second plurality of positions associated with the plurality of fiducials based upon the determined second position of the second fiducial;
   determining a second target position based upon the second plurality of positions;
   determining a relation to a boundary based upon the first target position and the second target position, wherein the relation to the boundary comprises a determination, during radiation therapy, that a centroid of the plurality of fiducials will traverse the boundary at a future time;
   associating a timestamp with the future time at which the centroid of the plurality of fiducials will traverse the boundary; and
   interrupting the radiation therapy at the future time associated with the timestamp.

2. The computer-implemented method of claim 1, wherein the first target position corresponds to a first centroid position and the second target position corresponds to a second centroid position.

3. The computer-implemented method of claim 1, wherein the first target position corresponds to a first centroid position by an offset defined in a patient plan.

4. The computer-implemented method of claim 1, the method further comprising maintaining a rigid body model of the set of the plurality of fiducials, and wherein determining a relation to a boundary comprises determining a centroid velocity.

5. The computer-implemented method of claim 1, wherein the relation to the boundary comprises a determination that a centroid of the plurality of fiducials has traversed the boundary.

6. The computer-implemented method of claim 1, the method further comprising determining an initial target orientation using a weighted, rigid, Procrustes fit.

7. The computer-implemented method of claim 1, the method further comprising performing a dynamic calibration measurement of the first fiducial to mitigate an effect of a LINAC gantry on localization accuracy, the dynamic calibration measurement comprising a measurement of the mutual inductance between all coils in an array.

8. The computer-implemented method of claim 1, further comprising:
   determining a third position of a third fiducial of the plurality of fiducials; and
   predicting a third plurality of positions associated with the plurality of fiducials based on a first predicted position of the second plurality of positions associated with the third fiducial.

9. The computer-implemented method of claim 1 wherein predicting the second plurality of positions associated with the plurality of fiducials is further based on a comparison between (1) a first predicted position of the first plurality of positions associated with the second fiducial and (2) the determined second position of the second fiducial.

10. A non-transitory computer-readable medium comprising instructions executable by one or more processors to perform a method comprising:
    determining a first position of a first fiducial of a plurality of fiducials, the plurality of fiducials located in or on a portion of a human body;
    predicting a first plurality of positions associated with the plurality of fiducials based upon the determined position of the first fiducial;
    determining a first target position based upon the first plurality of positions;
    determining a second position of a second fiducial of the plurality of fiducials;
    predicting a second plurality of positions associated with the plurality of fiducials based upon the determined second position of the second fiducial;
    determining a second target position based upon the second plurality of positions;
    determining a relation to a boundary based upon the first target position and the second target position, wherein the relation to the boundary comprises an inference, during treatment, that a centroid of the plurality of fiducials will traverse the boundary within a future period of time;
    associating a timestamp with a minimum time to boundary crossing of the future period of time; and
    interrupting treatment at the minimum time to boundary crossing associated with the timestamp.

11. The non-transitory computer-readable medium of claim 10, wherein the first target position corresponds to a first centroid position and the second target position corresponds to a second centroid position.

12. The non-transitory computer-readable medium of claim 10, wherein the first target position corresponds to a first centroid position by an offset defined in a patient plan.

13. The non-transitory computer-readable medium of claim 10, the method further comprising maintaining a rigid body model of the set of the plurality of fiducials, and wherein determining a relation to a boundary comprises determining a centroid velocity.

14. The non-transitory computer-readable medium of claim 10, wherein the relation to the boundary comprises a determination that a centroid of the plurality of fiducials has traversed the boundary.

15. The non-transitory computer-readable medium of claim 10, the method further comprising determining an initial target orientation using a weighted, rigid, Procrustes fit.

16. The non-transitory computer-readable medium of claim 10, the method further comprising performing a dynamic calibration measurement of the first fiducial to mitigate an effect of a LINAC gantry on localization accuracy, the dynamic calibration measurement comprising a measurement of the mutual inductance between all coils in an array.

17. A computer system comprising:
at least one processor;
at least one memory, the at least one memory comprising instructions configured to cause the computer system to perform a method using the at least one processor, the method comprising:
determining a first position of a first fiducial of a plurality of fiducials, the plurality of fiducials located in or on a portion of a human body;
predicting a first plurality of positions associated with the plurality of fiducials based upon the determined position of the first fiducial;
determining a first target position based upon the first plurality of positions;
determining a second position of a second fiducial of the plurality of fiducials;
predicting a second plurality of positions associated with the plurality of fiducials based upon the determined second position of the second fiducial;
determining a second target position based upon the second plurality of positions;
determining, during radiation therapy, a relation to a boundary based upon the first target position and the second target position, wherein the relation to the boundary comprises a prediction that a centroid of the plurality of fiducials will traverse the boundary at a future time;
associating a timestamp with the future time at which the centroid of the plurality of fiducials will traverse the boundary; and
interrupting the radiation therapy at the future time.

18. The computer system of claim 17, wherein the first target position corresponds to a first centroid position and the second target position corresponds to a second centroid position.

19. The computer system of claim 17, wherein the first target position corresponds to a first centroid position by an offset defined in a patient plan.

20. The computer system of claim 17, the method further comprising maintaining a rigid body model of the set of the plurality of fiducials, and wherein determining a relation to a boundary comprises determining a centroid velocity.

21. The computer system of claim 17, wherein the relation to the boundary comprises a determination that a centroid of the plurality of fiducials has traversed the boundary.

22. The computer system of claim 17, the method further comprising determining an initial target orientation using a weighted, rigid, Procrustes fit.

23. The computer system of claim 17, the method further comprising performing a dynamic calibration measurement of the first fiducial to mitigate an effect of a LINAC gantry on localization accuracy, the dynamic calibration measurement comprising a measurement of the mutual inductance between all coils in an array.

* * * * *